(12) United States Patent
Utley et al.

(10) Patent No.: US 7,699,844 B2
(45) Date of Patent: *Apr. 20, 2010

(54) METHOD FOR TREATING FECAL INCONTINENCE

(75) Inventors: David Utley, San Carlos, CA (US); Scott West, Livermore, CA (US); John Gaiser, Mountain View, CA (US); Rachel Croft, San Francisco, CA (US)

(73) Assignee: Mederi Therapeutics, Inc., Cos Cob, CT (US)

( * ) Notice: Subject to any disclaimer, the term of this patent is extended or adjusted under 35 U.S.C. 154(b) by 281 days.

This patent is subject to a terminal disclaimer.

(21) Appl. No.: 11/446,771

(22) Filed: Jun. 5, 2006

(65) Prior Publication Data
US 2006/0224157 A1 Oct. 5, 2006

Related U.S. Application Data

(62) Division of application No. 10/674,242, filed on Sep. 29, 2003, now Pat. No. 7,056,320, which is a division of application No. 09/556,169, filed on Apr. 21, 2000, now Pat. No. 6,645,201.

(60) Provisional application No. 60/143,749, filed on Jul. 14, 1999.

(51) Int. Cl.
*A61B 18/18* (2006.01)
(52) U.S. Cl. .......................... 606/41; 128/898
(58) Field of Classification Search .............. 606/41, 606/45, 39, 47; 604/506, 22; 607/96, 98–102; 600/29–32
See application file for complete search history.

(56) References Cited

U.S. PATENT DOCUMENTS

| | | | |
|---|---|---|---|
| 2,382,109 A | | 8/1945 | Sheiffele |
| 4,813,422 A | * | 3/1989 | Fisher et al. ............... 600/473 |
| 5,259,388 A | * | 11/1993 | Eisman et al. ............. 600/546 |
| 5,370,675 A | | 12/1994 | Edwards et al. |
| 5,403,311 A | | 4/1995 | Abele et al. |
| 5,451,223 A | | 9/1995 | Ben-Simhon |
| 5,452,719 A | * | 9/1995 | Eisman et al. ............. 600/373 |
| 5,709,224 A | | 1/1998 | Behl et al. |
| 5,827,276 A | | 10/1998 | LeVeen et al. |
| 5,849,011 A | | 12/1998 | Jones et al. |
| 5,873,877 A | | 2/1999 | McGaffigan et al. |

(Continued)

FOREIGN PATENT DOCUMENTS

| WO | WO 98/11834 | 3/1998 |
|---|---|---|
| WO | WO 00/59393 | 10/2000 |

*Primary Examiner*—Michael Peffley
*Assistant Examiner*—Samantha Muro
(74) *Attorney, Agent, or Firm*—Ryan Kromholz & Manion, S.C.

(57) ABSTRACT

A sphincter tissue region is treated using a support structure sized for advancement into the anal canal. At least one electrode is carried by the structure. A mechanism is coupled to the electrode to move the electrode between a first position retracted in the support structure and a second position extended from the support structure through surface tissue to penetrate a subsurface tissue region at or near a sphincter in the anal canal. A cable is coupled to the electrode to conduct energy for application by the electrode to form a lesion in the subsurface tissue region.

3 Claims, 26 Drawing Sheets

U.S. PATENT DOCUMENTS

| | | |
|---|---|---|
| 6,009,877 A | 1/2000 | Edwards |
| 6,014,589 A | 1/2000 | Farley et al. |
| 6,017,338 A | 1/2000 | Brucker et al. |
| 6,051,017 A * | 4/2000 | Loeb et al. ............ 607/1 |
| 6,056,744 A | 5/2000 | Edwards |
| 6,077,257 A * | 6/2000 | Edwards et al. ............ 604/506 |
| 6,092,528 A | 7/2000 | Edwards |
| 6,156,032 A * | 12/2000 | Lennox ............ 606/41 |
| 6,159,170 A * | 12/2000 | Borodulin et al. ............ 601/46 |
| 6,231,571 B1 | 5/2001 | Ellman et al. |
| 6,325,798 B1 | 12/2001 | Edwards et al. |
| 6,407,308 B1 * | 6/2002 | Roe et al. ............ 604/361 |
| 6,419,673 B1 | 7/2002 | Edwards et al. |
| 6,645,201 B1 * | 11/2003 | Utley et al. ............ 606/41 |
| 6,743,197 B1 * | 6/2004 | Edwards ............ 604/103.01 |
| 7,022,105 B1 * | 4/2006 | Edwards ............ 604/103.01 |
| 7,056,320 B2 * | 6/2006 | Utley et al. ............ 606/41 |

\* cited by examiner

FIG. 6A
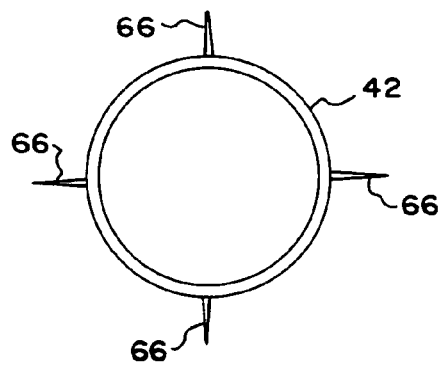
FIG. 6B
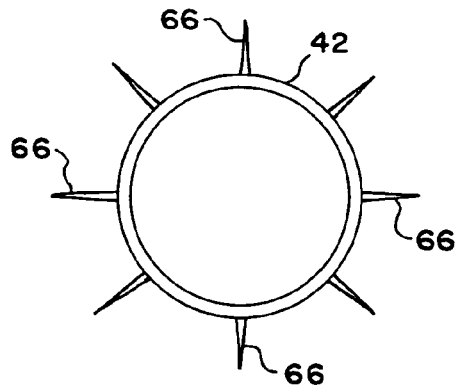
FIG. 6C
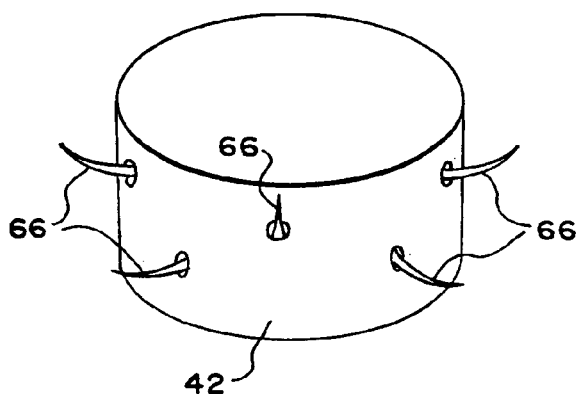
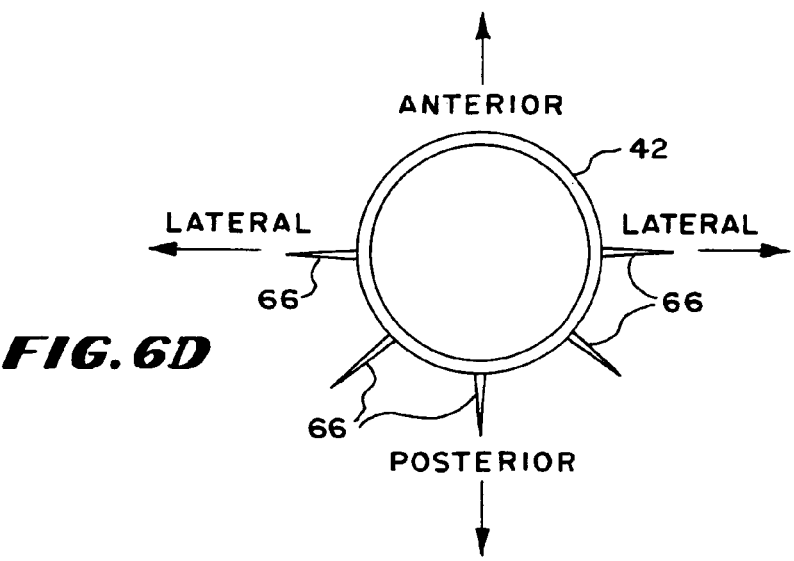
FIG. 6D

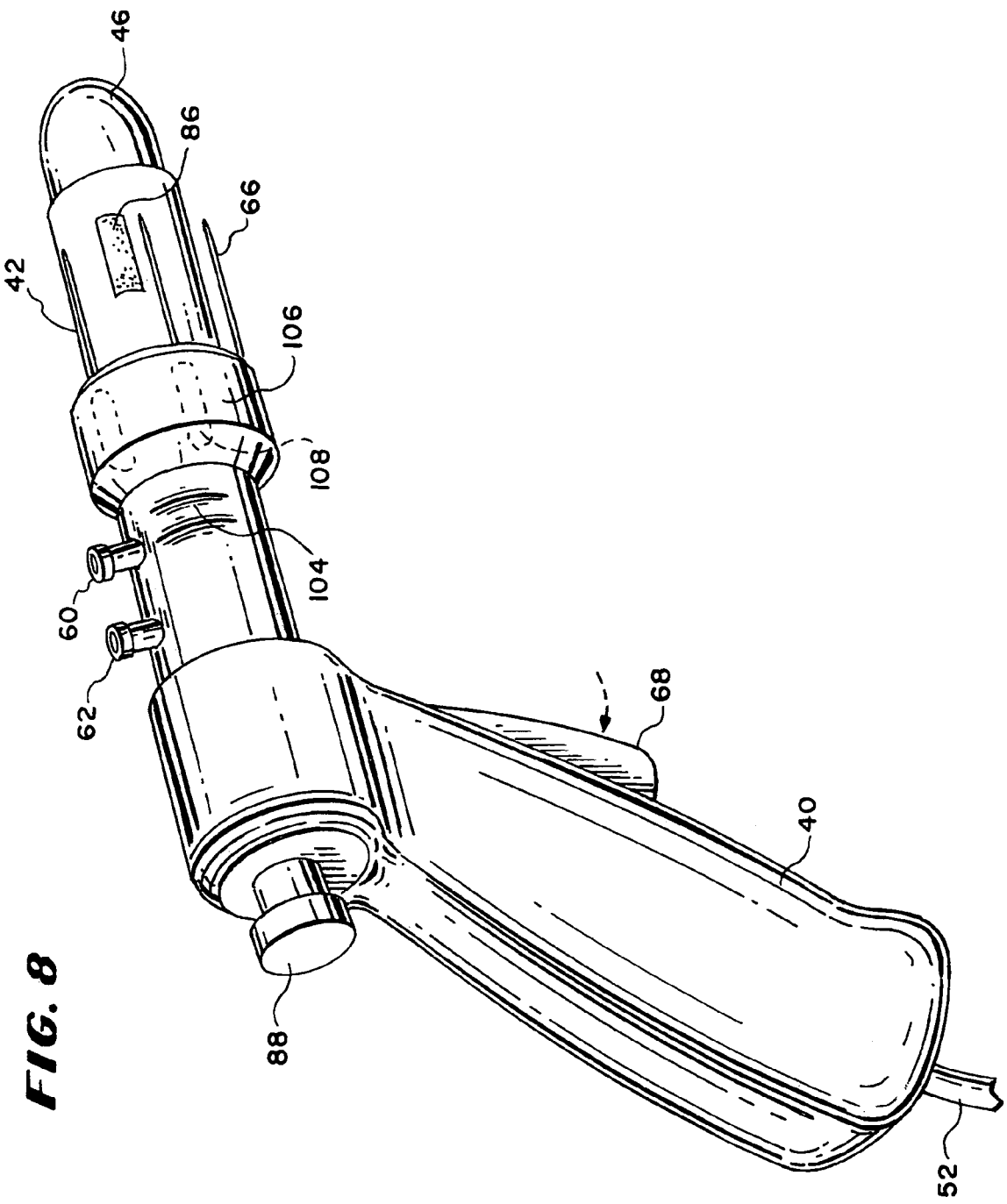

METHOD FOR TREATING FECAL INCONTINENCE

RELATED APPLICATIONS

This application is a divisional of U.S. patent application Ser. No. 10/674,242, filed Sep. 29, 2003, now U.S. Pat. No. 7,056,320, which is a divisional of U.S. patent application Ser. No. 09/556,169, filed Apr. 21, 2000, now U.S. Pat. No. 6,645,201, which claims the benefit of U.S. Provisional Patent Application Ser. No. 60/143,749, filed Jul. 14, 1999, and entitled "Systems and Methods for Treating Dysfunctions in the Intestines and Rectum," which is incorporated herein by reference.

FIELD OF THE INVENTION

In a general sense, the invention is directed to systems and methods for treating interior tissue regions of the body. More specifically, the invention is directed to systems and methods for treating dysfunction in the intestines and rectum.

BACKGROUND OF THE INVENTION

The gastrointestinal tract, also called the alimentary canal, is a long tube through which food is taken into the body and digested. The alimentary canal begins at the mouth, and includes the pharynx, esophagus, stomach, small and large intestines, and rectum. In human beings, this passage is about 30 feet (9 meters) long.

Small, ring-like muscles, called sphincters, surround portions of the alimentary canal. In a healthy person, these muscles contract or tighten in a coordinated fashion during eating and the ensuing digestive process, to temporarily close off one region of the alimentary canal from another region of the alimentary canal.

In the rectum, two muscular rings, called the internal and external sphincter muscles, normally keep fecal material from leaving the anal canal. The external sphincter muscle is a voluntary muscle, and the internal sphincter muscle is an involuntary muscle. Together, by voluntary and involuntary action, these muscles normally contract to keep fecal material in the anal canal.

The rectum can stretch and hold fecal material for some time after a person becomes aware that the material is there. The holding action of these sphincter muscles is critical in maintaining fecal continence.

Damage to the external or internal sphincter muscles can cause these sphincters to dysfunction or otherwise lose their tone, such that they can no longer sustain the essential fecal holding action. Fecal incontinence results, as fecal material can descend through the anal canal without warning, stimulating the sudden urge to defecate.

The recurring sensation of uncontrolled fecal urgency alone can produce significant, negative impact on lifestyle. The physical effects of fecal incontinence (i.e., the loss of normal control of the bowels and gas, liquid, and solid stool leakage from the rectum at unexpected times) can also cause embarrassment, shame, and a loss of confidence, and can further lead to mental depression.

Fecal incontinence affects as many as one million Americans. It is more common in women and in the elderly of both sexes. Many people with fecal incontinence are ashamed to talk about their problem with their doctor or family.

In women, damage to the external or internal sphincter muscle can occur during childbirth. It is especially likely to happen in a difficult delivery that uses forceps and/or an episiotomy. Muscle damage can also occur as a result of trauma, or during rectal surgery. It may also occur in people with inflammatory bowel disease or an abscess in the perirectal area.

Young people suffering damage to these sphincters in the rectum can often compensate for the muscle weakness to avoid incontinence. However, they typically develop incontinence in later life, as their muscles grow weaker and the supporting structures in the pelvis become loose.

There are non-surgical ways to treat fecal incontinence. For example, dietary bulking agents or other antimotility agents (like fats) can be used to change the texture of fecal material, to slow its descent through the rectum. Biofeedback therapy has met with success. Still, this therapy is time consuming and works to overcome dysfunction only of the voluntary external sphincter muscle. Biofeedback therapy is not effective in overcoming dysfunction of the involuntary internal sphincter muscle.

There are also various surgical options for treating fecal incontinence. These surgical options include, for example, Parks post-anal repair, encirclement (using Tiersch wire or gracilis muscle), overlapping sphincteroplasty and levatoroplasty, gluteus muscle transposition, colostomy, gracilis muscle stimulated neosphinter, and artificial bowel sphincters.

Other abnormal, uncomfortable or debilitating conditions can occur in the rectum and adjoining intestines, which require treatment or surgical intervention. For example, cancer often arises in polyps, small noncancerous growths in the intestine. A tendency to develop polyps is probably influenced by genes. Regardless, it is a common practice to remove polyps, when discovered.

Many people also suffer hemorrhoids, or piles. Hemorrhoids are enlargements of the veins of the rectum. Many people seem to inherit a tendency toward developing hemorrhoids. However, any condition that causes prolonged or repeated increases in the blood pressure in the rectal veins may contribute to the development of hemorrhoids. Such conditions include constipation, pregnancy, and long periods of standing. Hemorrhoids can be internal (protruding through the anal sphincter) or external (covered with skin outside the sphincter). Hemorrhoids of the external veins usually cause little discomfort, unless a blood clot forms in the affected vein and results in inflammation. Hemorrhoids of the internal veins may bleed or descend through the anus as a result of bowel movements. Such hemorrhoids may cause pain or itching. Mild cases can be treated with medicated ointments or suppositories (inserted capsules), or by soaking in warm water. If the victim repeatedly suffers painful attacks or bleeding, a physician may remove the hemorrhoids surgically. However, surgery for hemorrhoids can itself damage the external or internal sphincter muscle and lead to fecal incontinence.

SUMMARY OF THE INVENTION

The invention provides a method for treating fecal incontinence. The method inserts a transparent structure into an anal cavity. The method visualizes from outside the anal cavity a dentate line within the anal canal through the transparent structure. While visualizing the dentate line, the method advances at least one electrode into tissue at or near an anal sphincter above the dentate line. The method applies energy through the electrode to create a lesion in the sphincter. The method conveys fluid into contact with the tissue to cool the tissue while applying energy to the electrode.

Features and advantages of the inventions are set forth in the following Description and Drawings.

BRIEF DESCRIPTION OF THE DRAWINGS

FIG. 6A is a top view of the barrel of the treatment device shown in FIGS. 3 and 4, showing a symmetrical, circumferentially spaced array of four energy application electrodes;

FIG. 6B is a top view of the barrel of the treatment device shown in FIGS. 3 and 4, showing a symmetrical, circumferentially spaced array of eight energy application electrodes;

FIG. 6C is a side view of the barrel of the treatment device shown in FIGS. 3 and 4, showing a symmetrical, circumferentially spaced array of eight energy application electrodes in two axially spaced apart rings;

FIG. 6D is a top view of the barrel of the treatment device shown in FIGS. 3 and 4, showing an asymmetrical, circumferentially spaced array of five energy application electrodes;

FIG. 8 is a perspective view of the treatment device shown in FIG. 7, with the straight energy application electrodes extended for use;

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

This Specification discloses various catheter-based systems and methods for treating dysfunction of sphincters and adjoining tissue regions in the body. The systems and methods are particularly well suited for treating these dysfunctions in the lower gastrointestinal tract, e.g., in the intestines, rectum and anal canal. For this reason, the systems and methods will be described in this context.

Still, it should be appreciated that the disclosed systems and methods are applicable for use in treating other dysfunctions elsewhere in the body, e.g., for restoring compliance to or otherwise tightening interior tissue or muscle regions. The systems and methods that embody features of the invention are also adaptable for use with systems and surgical techniques that are not necessarily catheter-based.

I. Anatomy of the Rectum and Anal Canal

Figure 1:
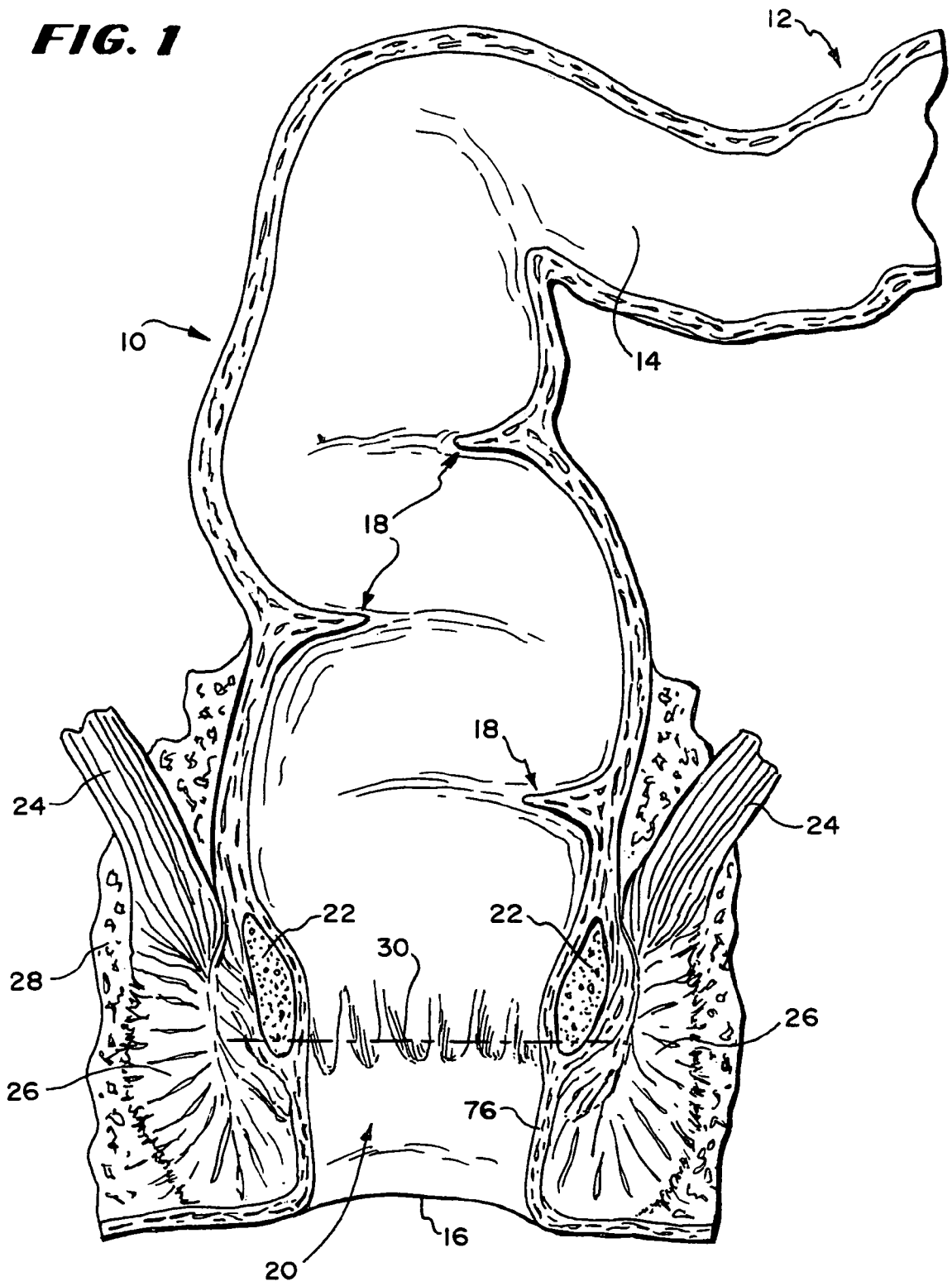
FIG. 1 is an anatomic view of the rectum and anal canal.

As FIG. 1 shows, the rectum is the terminal part of the large intestine 12. The rectum 10 extends from the sigmoid flexure 14 (which is the narrowest part of the colon) to the anal orifice 16. The rectum 10 is about 15 to 17 cm in overall length.

The upper or superior portion of the rectum 10 extends downward from the sigmoid flexure 14. This portion of the rectum 10 is almost completely surrounded by the peritoneum. A mucous membrane lines this portion of the rectum 10. The mucous membrane is thicker, of a darker color, and more vascular than elsewhere in the colon.

The superior portion of the rectum 10 contains a number of permanent folds of a semilunar shape, which are called the Houston valves 18. As FIG. 1 shows, there are usually three Houston valves 18. Sometimes a fourth is present, and occasionally only two are found.

When the rectum 10 is empty, the Houston valves 18 overlap each other. The valves 18 support the weight of fecal matter, to slow its descent toward the anal orifice 16. When the inferior or lower part of the rectum 10 is contracted to expel fecal matter, a number of additional folds develop in the mucous membrane of the superior portion of the rectum 10, to urge fecal matter downward.

The middle portion of the rectum 10 is covered anteriorly and laterally by peritoneum as it extends from the superior portion. However, as the rectum 10 extends further downward, the lateral peritoneum gradually recedes.

The lower or inferior portion of the rectum 10 is called the anal canal 20. It typically extends about 4 to 5 cm above the anal orifice 16. The anal canal 20 is invested by the internal sphincter muscle 22, supported by the Levatores ani muscle 24, and surrounded at its termination by the external sphincter muscle 26. The fat of the ischio-rectal fossae 28 laterally surrounds the anal canal 20.

The external sphincter muscle 26 is a thin flat plane of muscular fibers, measuring about 5 cm in length. It is always in a state of tonic contraction to keep the anal orifice 16 closed. In an empty condition, the anal canal 20 therefore has the appearance of a longitudinal slit. The external sphincter muscle 26 can voluntarily be placed in a greater condition of contraction, to more firmly occlude the anal orifice 16.

The internal sphincter muscle 22 is a muscular ring that surrounds the lower extremity of the rectum 10 for about 2 cm. Its inferior border is contiguous with the external sphincter muscle 26. However, the functions of the two sphincter muscles 22 and 26 are separate. Unlike the external sphincter muscle 26, the internal sphincter muscle 22 is an involuntary muscle. Together, the voluntary external sphincter muscle 26 works with the involuntary internal sphincter muscle 22 to occlude the anal orifice 16. The internal sphincter muscle 22 contributes about 85% of the resting tone of the anal canal 20, to keep fecal material in the rectum 10 until time of controlled expulsion.

The levator ani muscle 24 is a broad, thin muscle situated on each side of the pelvis. This muscle supports the lower end of the rectum 10 and bladder during the controlled efforts of expulsion. A pectinate (dentate) line 30 is defined about 2.5 to 3 cm above the anal orifice 16. The superior extent of the external sphincter muscle 26 extends about 5 cm above the pectinate (dentate) line 30. The superior extent of the internal sphincter muscle 22 extends about 2 to 2.5 cm above the pectinate (dentate) line.

Sensitive mucosal tissue, called the anoderm, lines the anal canal 20 below the pectinate line 30. Anoderm tissue is sensitive to contact with fecal material. When contacting anoderm tissue, the sensed presence of fecal material excites a sensation demanding discharge.

Mucosal tissue immediately above the pectinate line 30, called the anal columns, is also sensitive to the presence of fecal material. The anal columns provide sensory information that discriminates among different types and textures of fecal material, thereby aiding in overall control of the discharge of fecal material.

Because of their important sensory functions, treatment of the rectum 10 should guard against damage to the mucosal tissue below and above the pectinate (dentate) line 30. This sensitive mucosal tissue may be damaged, e.g., by exposure to abnormal heat, and typically do not regenerate after thermal injury.

In a person suffering from fecal incontinence, the external sphincter muscle 26, or the internal sphincter muscle 22, or both lose their tone. As a result, the anal orifice 16 is not occluded. Fecal material descends without control, to spontaneously excite the sensitive anoderm tissue to demand immediate discharge.

It should be noted that the views of the rectum 10 and anal canal 20 shown in FIG. 1, and elsewhere in the drawings, are not intended to be strictly accurate in an anatomic sense. The drawings show the rectum 10 and anal canal 20 in somewhat diagrammatic form to demonstrate the features of the invention.

II. System for Treating Fecal Incontinence

Figure 2:
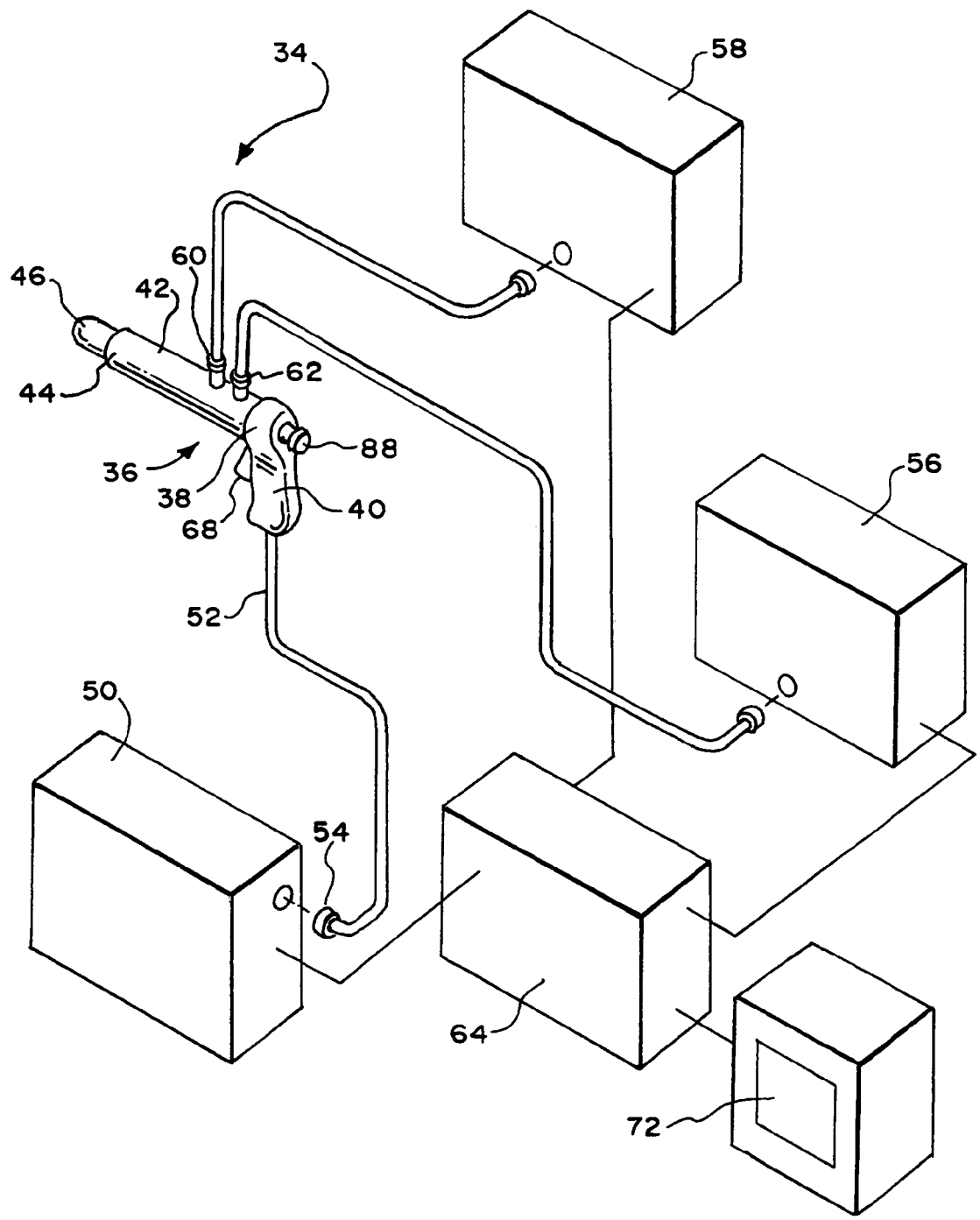
FIG. 2 is a diagrammatic view of a system for treating sphincters and adjoining tissue regions in the rectum and anal canal.

FIG. 2 shows a system 34 for treating dysfunction of the external sphincter muscle 26, or internal sphincter muscle 22, or both.

A. Hand Gripped Treatment Device

Figure 3:
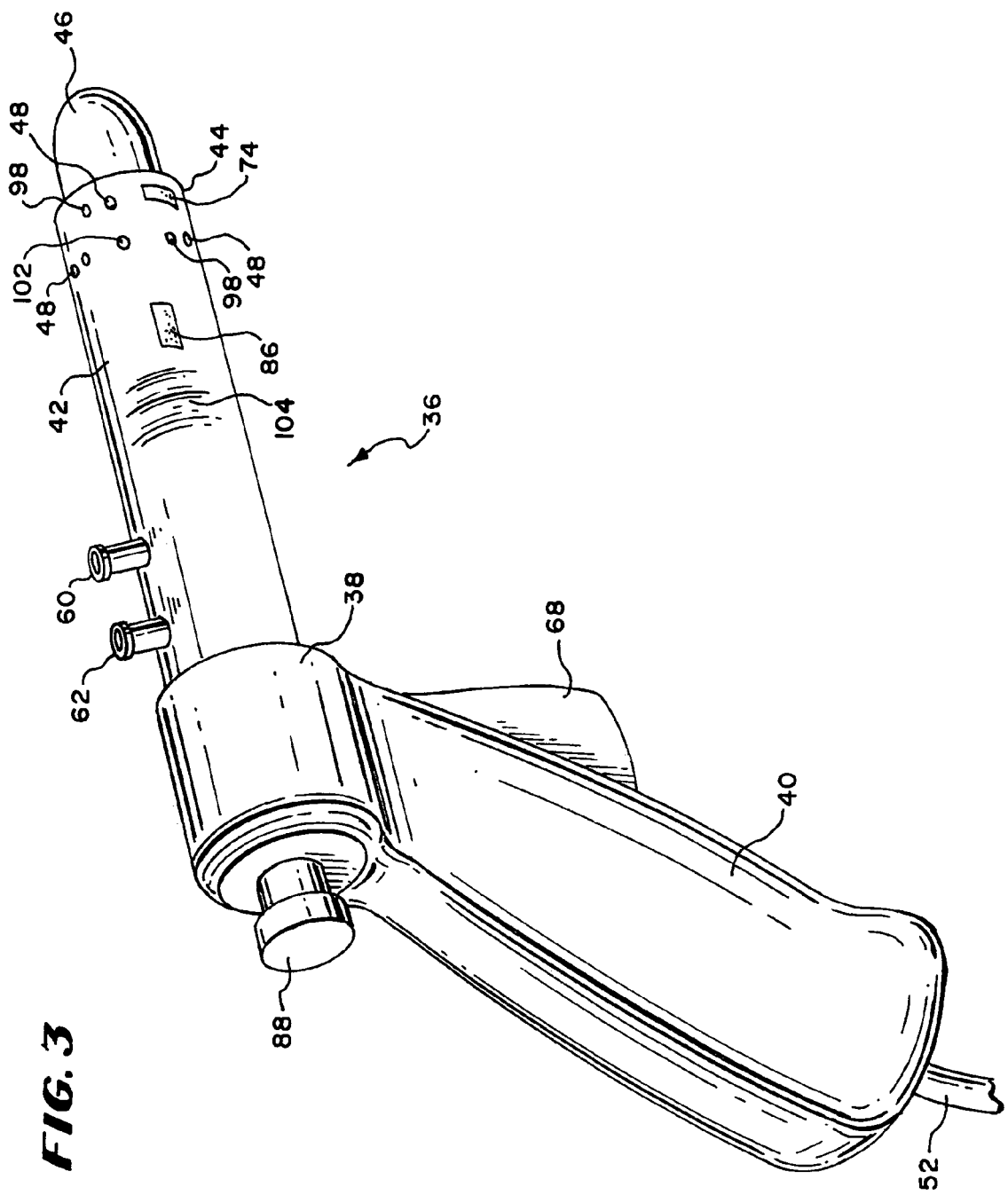
FIG. 3 is a perspective view of a treatment device usable in association with the system shown in FIG. 2, with the energy application electrodes withdrawn for deployment.

The system 34 includes a treatment device 36. The device 36 can be constructed in various ways. In FIG. 3, the device 36 includes a hand piece 38 made, e.g., from molded plastic. The hand piece 38 includes a handle grip 40, which is sized to be conveniently held by a physician, in the same fashion as an anuscope.

The hand piece 38 also includes a barrel 42 having a distal end 44. A bullet-shaped introducer 46 extends a distance beyond the distal end 44. The barrel 42 and introducer 46 are sized (e.g., by having a maximum outside diameter of about 30 mm to 33 mm) for insertion into the rectum 10 through the anal orifice 16. The introducer 46 aids passage through the anal canal 20. The introducer 46 can be mounted for movement within the barrel 42 and coupled to a push-pull actuator 88. In this arrangement, the introducer 42 can be removed from the barrel 42 once the barrel 42 has passed through the anal canal 20 and is deployed in the rectum 10.

The barrel 42 can include malleable sections 104 to allow the distal end 44 of the barrel 42 to be bent relative to the hand grip 40, either left or right, or up and down, or both, thereby aiding manipulation. Further details of using the treatment device 36 will be described later.

The hand grip 40, barrel 42, and introducer 46 can form an integrated construction intended for a single use and subsequent disposal as a unit. Alternatively, the hand grip 40 can comprise a nondisposable component intended for multiple uses. In this arrangement, the barrel 42 and introducer 46, along with other components carried by the barrel 42 (as will be described), comprise a disposable assembly, which the physician releasably connects to the hand grip 40 at time of use and disconnects and discards after use. The proximal end of the barrel 42 can, for example, include a male plug connector that couples to a female plug receptacle on the hand grip 40.

Figure 4:
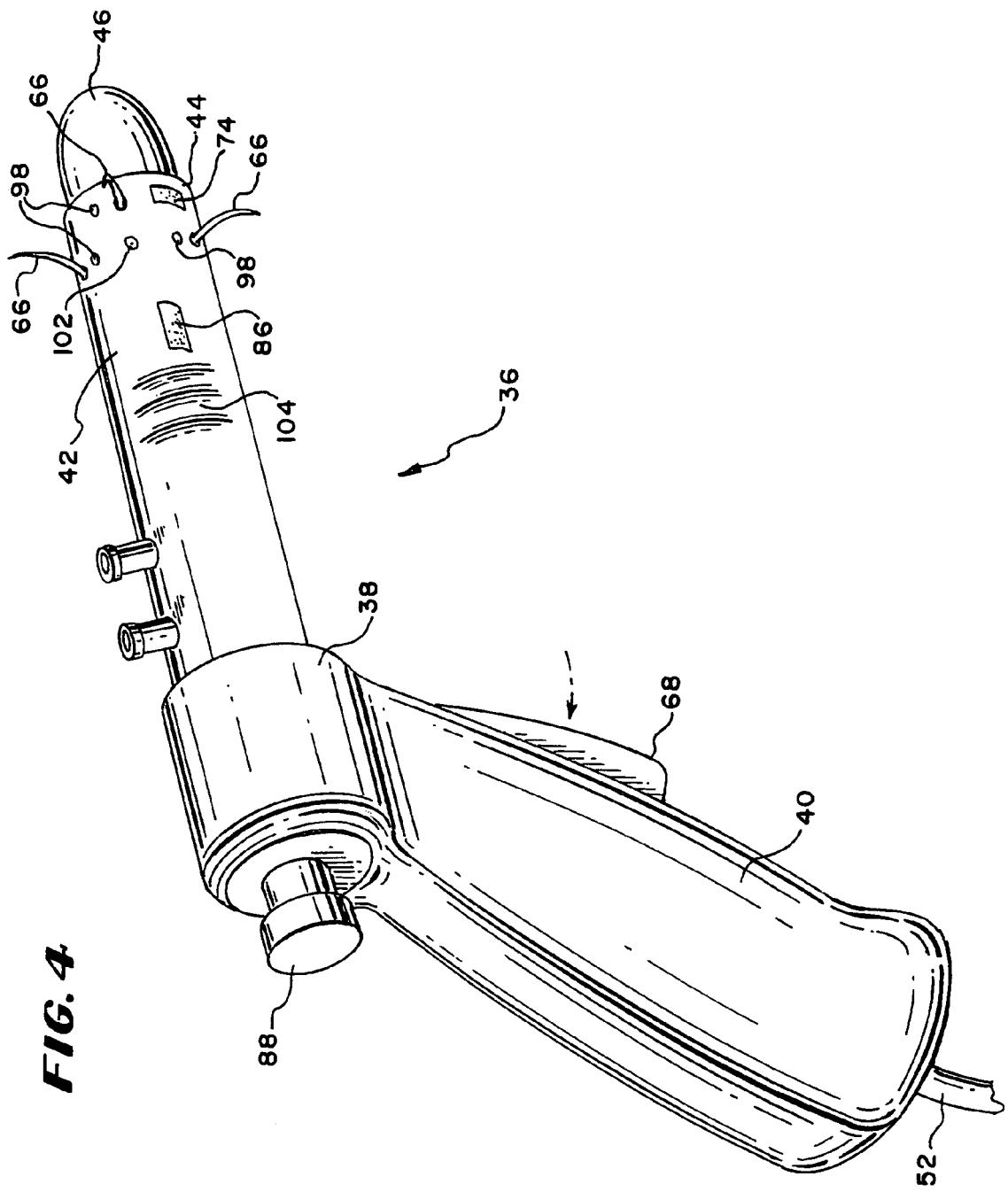
FIG. 4 is a perspective view of the treatment device shown in FIG. 3, with the energy application electrodes extended for use.

The barrel 42 carries an array of energy applicators 66 at its distal end 44. The energy applicators 66 slide through openings 48 in the barrel 42 between a retracted position, withdrawn in the barrel 42 (shown in FIG. 3) and an extended position, extending outward from the barrel 42 (shown in FIG. 4).

A trigger or other push-pull lever 68 on the hand grip 40 is coupled through the barrel 42 to the energy applicators 66. The lever 68 controls movement of the energy applicators 66 between the retracted position (by pushing forward on the lever 68) and the extended position (by pulling rearward on the lever 68).

The applicators 66 apply energy in a selective fashion to a targeted sphincter region below mucosal tissue in the rectum 10. The applied energy creates one or more lesions, or a prescribed pattern of lesions, below the mucosal surface 76 of the rectum 10. The submucosal lesions are formed in a manner that preserves and protects the exterior mucosal tissue against damage.

It has been discovered that natural healing of the subsurface lesions in the rectum can lead to a physical tightening of the external or internal sphincter muscle 22 or 26, or both muscles 22 and 26. The physical tightening of one or both of these muscles 22 or 26 can restore normal closure function, thereby providing therapy for fecal incontinence.

In this arrangement, the system 34 includes a generator 50 to supply the treatment energy. In the illustrated embodiment, the generator 50 supplies radio frequency energy, e.g., having a frequency in the range of about 400 kHz to about 10 mHz. In this arrangement, the energy applicators 66 comprise radio frequency transmitting electrodes.

The electrodes 66 can be formed from various energy transmitting materials. In the illustrated embodiment, for deployment in the rectum 10 and anal canal 20, the electrodes 66 are formed from nickel titanium. The electrodes 66 can also be formed from stainless steel, e.g., 304 stainless steel, or, a combination of nickel titanium and stainless steel.

In the illustrated embodiment, the electrodes 66 have sufficient distal sharpness and strength to penetrate a desired depth into the internal and/or external sphincter muscle 22 and/or 26. The desired depth can range from about 7 mm to about 8 mm from the inside wall of the rectum 10.

Of course, other forms of energy can be applied, e.g., coherent or incoherent light; heated or cooled fluid; resistive heating; microwave; ultrasound; a tissue ablation fluid; or cryogenic fluid. The form and fit of the energy applicators 66 will, of course, differ to accommodate application of other forms of energy.

B. Auxiliary System Components

In the illustrated embodiment, a cable 52 extending from the proximal end of the hand grip 40 terminates with an electrical connector 54. The cable 52 is electrically coupled to the electrodes 66, e.g., by wires that extend through the interior of the hand grip 40 and barrel 42. The connector 54 plugs into the generator 50, to convey the generated energy to the electrodes 66.

The system 34 also includes certain auxiliary processing equipment. In the illustrated embodiment, the processing equipment comprises an external fluid delivery apparatus 56 and an external aspirating apparatus 58.

The barrel 42 includes one or more interior lumens (not shown) that terminate in fittings 60 and 62, located on the hand grip 40 or barrel 42. One fitting 60 connects to the fluid delivery apparatus 56, to convey processing fluid for discharge by or near the electrodes 66. The other fitting 62 connects to the aspirating apparatus 58, to convey aspirated material from or near from the distal end 44 of the barrel 42 for discharge.

The system 34 also includes a controller 64. The controller 64, which preferably includes a central processing unit (CPU), is linked to the generator 50, the fluid delivery apparatus 56, and the aspirating apparatus 58. Alternatively, the aspirating apparatus 58 can comprise a conventional vacuum source typically present in a physician's suite, which operates continuously, independent of the controller 64.

The controller 64 governs the power levels, cycles, and duration that the radio frequency energy is distributed to the electrodes 66, to achieve and maintain power levels appropriate to achieve the desired treatment objectives. In tandem, the controller 64 also governs the delivery of processing fluid and, if desired, the removal of aspirated material.

The controller 64 includes an input/output (I/O) device 72. The I/O device 72 allows the physician to input control and processing variables, to enable the controller to generate appropriate command signals. The I/O device 72 also receives real time processing feedback information from one or more sensors associated with the operative element (as will be described later), for processing by the controller 64, e.g., to govern the application of energy and the delivery of processing fluid. The I/O device 72 can also include a graphical user interface (GUI), to graphically present processing information to the physician for viewing or analysis.

C. Deployment of the Electrodes (i) Biased, Bent Electrodes

Figure 5:
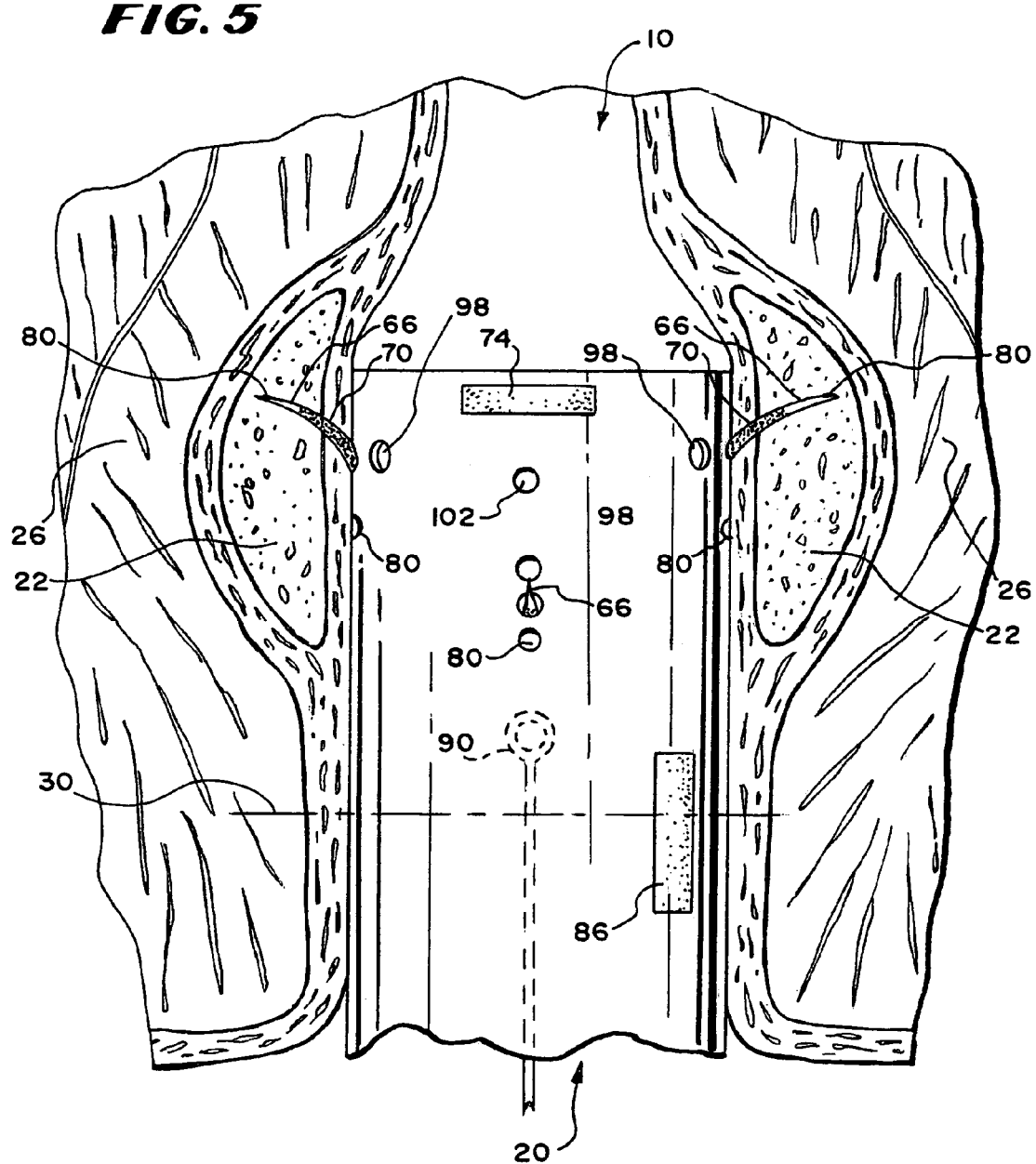
FIG. 5 is an anatomic view of the anal canal, with the treatment device shown in FIGS. 3 and 4 with the energy application electrodes extended into the internal sphincter muscle.

In the embodiment shown in FIG. 5, to facilitate penetration and anchoring in the rectum 10, each electrode 66 is biased with a bend. Movement of the electrode 66 into the barrel 42 overcomes the bias and straightens the electrode 66.

In the illustrated embodiment, each electrode 66 is normally biased with an antegrade bend (i.e., bending toward the proximal base of the barrel 42). Alternatively, each electrode 66 can be normally biased toward an opposite retrograde bend (i.e., bending toward the introducer 46).

As FIG. 5 shows, an electrical insulating material 70 is coated about the proximal end of each electrode 66. For deployment in the rectum 10, the length of the material 70 ranges from about 80 to about 120 mm. The insulating material 70 can comprise, e.g., a Polyethylene Terephthalate (PET) material, or a polyimide or polyamide material. For deployment in the rectum 10, each electrode 66 preferably presents an exposed, non-insulated conductive length of about 8 mm, providing an exposed surface area at the distal end of each electrode 66 of preferably about 16 mm$^2$.

When penetrating the internal or external sphincter muscles, the distal end of the electrode 66 transmits radio frequency energy. The material 70 insulates the mucosal surface 76 of the rectum 10 from direct exposure to the radio frequency energy. Thermal damage to the mucosal surface 76 is thereby avoided. As will be described later, the mucosal surface 76 can also be actively cooled during application of radio frequency energy, to further protect it from thermal damage.

The surface area of the exposed region on the electrodes 66 affects the impedance of the electrodes 66 during use. Generally speaking, the larger the surface area of the exposed region is, the lower the expected impedance value is, leading to a fewer incidences of power shut-offs due to high impedance.

In the illustrated embodiment (see FIG. 6A), the barrel 42 deploys four electrodes 66, which are equally circumferentially spaced about the distal end 44. The electrodes 66 are arranged so that one opposing pair of electrodes 66 are axially spaced from the other opposing pair of electrodes 66 by about 1 cm (see FIG. 5).

Of course, a greater or lesser number of electrodes 66 can be present, and the geometric array of the electrodes 66 on the barrel 42 can vary. For example (see FIG. 6B), eight electrodes 66 can be circumferentially arranged about the distal end 44, either in a single ring or in an axially spaced relationship, shown in FIG. 6C. In FIG. 6C the electrodes 66 form two rows, each with four circumferentially spaced electrodes, which are axially spaced apart by about 1 cm. This arrangement makes possible the simultaneous formation of two lesion rings, one above and one below the pectinate (dentate) line.

As FIG. 6D shows, the electrodes 66 may be arranged in an asymmetric fashion, for deployment in a posterior or lateral direction, or both, but not in an anterior direction. This is because the anterior border of the anal canal 20 is close to the urethra and, in the female, the lower end of the vagina.

The controller 64 can condition the electrodes 66 to operate in a monopolar mode. In this arrangement, each electrode 66 serves as a transmitter of energy, and an indifferent patch electrode (not shown) serves as a common return for all electrodes 66.

Alternatively, the controller 64 can condition selected pairs of electrodes 66 to operate in a bipolar mode. In this mode, one of the electrodes comprises the transmitter and the other electrode comprises the return for the transmitted energy. The bipolar electrode pairs can comprise adjacent side-by-side pairs of electrodes 66 on the barrel 42, or electrodes 66 spaced more widely apart on the barrel 42.

In the illustrated embodiment (see FIG. 5), the barrel 42 carries at least one temperature sensor 80 in association with each electrode 66. In the embodiment illustrated in FIG. 5, each electrode 66 carries a temperature sensor 80 to sense temperature conditions near the exposed distal end of the electrode 66. The barrel 42 carries another temperature sensor 80 near the electrode 66 to sense tissue surface temperature conditions. One or more temperature sensors 80 can be located elsewhere, for example, in the insulation material 70.

In use, as the patient lies prone face down or on one side, the physician grasps the hand grip 40 and guides the introducer 46 and barrel 42 into the anal canal 20 through the anal orifice 16. The electrodes 66 are maintained in their retracted position during this initial stage of deployment.

The physician advances the introducer 46 and barrel 42 in the anal canal 20 to position the distal end 44 of the barrel 42 at a desired location above the pectinate (dentate) line 30. If the physician seeks to treat the internal sphincter muscle 22 (as FIG. 5 shows), the desired location is about 3 cm above the pectinate (dentate) line 30. If the physician seeks to treat the external sphincter muscle 26, the desired location is about 3.5 to 5 cm above the pectinate (dentate) line 30. Either location provides sufficient spacing to avoid thermal damage to the anoderm and anal columns during treatment of the targeted sphincter muscle. Typically, however, the voluntary, external sphincter muscle 26 need not be targeted for treatment.

Once the barrel 42 has passed into the anal canal 20, the physician can remove the introducer 46 by pulling on the actuator 88. With the introducer 46 removed, the physician visualizes the pectinate (detente) line 30 by looking down through the barrel 42. In this arrangement, at least the distal end 44 of the barrel 42 is made of a transparent material or includes a visualization slot 86 (see FIGS. 3 and 4), to enable the physician to view tissue from within the barrel 42. A fiberoptic 90 can also be inserted into the barrel 42 (see FIG. 5) to provide local illumination, or the physician can wear a headlamp for this purpose. The location of the electrodes 66 can also be marked on the inside of the barrel 42 to aid the physician in their alignment at the desired tissue location.

The barrel 42 or introducer 46 can also carry an ultrasound transducer 74 adjacent the distal end 44. The physician can then observe the anorectal echo as a real time image, as the distal end 44 is advanced into position. The real time image reflects the thickness of the mucosa and muscle wall.

An ultrasonic probe can also be inserted before and after deployment of the device 36. In this arrangement, the ultrasonic probe assesses the targeted tissue morphology before insertion of the device 36 and images the lesion location and depth after removal of the device 36.

Once the distal end 44 is located at the targeted site, the physician pulls rearward on the lever 68 to move the electrodes 66 into their extended position. The electrodes 66 pierce and pass through the mucosal tissue into the muscle tissue of the target sphincter muscle.

Given the arrangement of electrodes 66 shown in FIG. 6A, and with the distal end 44 located as shown in FIG. 5, the electrodes 66 penetrate the involuntary, internal sphincter muscle 22.

The physician commands the controller 64 to apply radio frequency energy through the electrodes 66. The energy can be applied simultaneously by all pairs of electrodes 66, or in any desired sequence. The energy ohmically heats the muscle tissue. The controller 64 samples temperatures sensed by the sensors 80 to control the application of energy. The controller 64 processes the sensed temperatures in a feedback loop to control the application of energy. The GUI can also display the sensed temperatures and the applied energy levels. Alternatively, the physician can manually control the energy levels based upon the temperature conditions displayed on the GUI. Changes in the anorectal echo as the procedure progresses also allows the physician to visualize lesion formation on a real time basis.

Preferably, energy is applied to achieve tissue temperatures in the targeted muscle tissue in the range of 55° C. to 95° C. In this way, lesions can typically be created at depths ranging from one to four millimeters below the mucosal surface 76. Typical energies range, e.g., between 100 and 1000 joules per electrode 66.

It is desirable that the lesions possess sufficient volume to evoke tissue healing processes accompanied by intervention of fibroblasts, myofibroblasts, macrophages, and other cells. The healing processes results in a contraction of tissue about the lesion, to decrease its volume or otherwise alter its biomechanical properties. The healing processes naturally tighten the muscle tissue in the sphincter muscle. To create greater lesion density in a given targeted tissue area, it is also desirable to create a pattern of multiple lesions, as the eight electrode pattern shown provides.

In one embodiment, the barrel 42 includes one or more lumens 98 (see FIG. 5). The fluid delivery apparatus 56 conveys processing fluid F through the lumen 98 for discharge at the treatment site. The processing fluid F can comprise, e.g., saline or sterile water, to cool the mucosal surface 76 while energy is being applied by the electrode 66 to ohmically heat muscle beneath the surface.

The aspirating apparatus 58 draws aspirated material and the processing fluid through another lumen 102 in the barrel 42 for discharge. This arrangement provides self-contained aspiration for the treatment device 36.

(ii) Straight Electrodes

Figure 7:
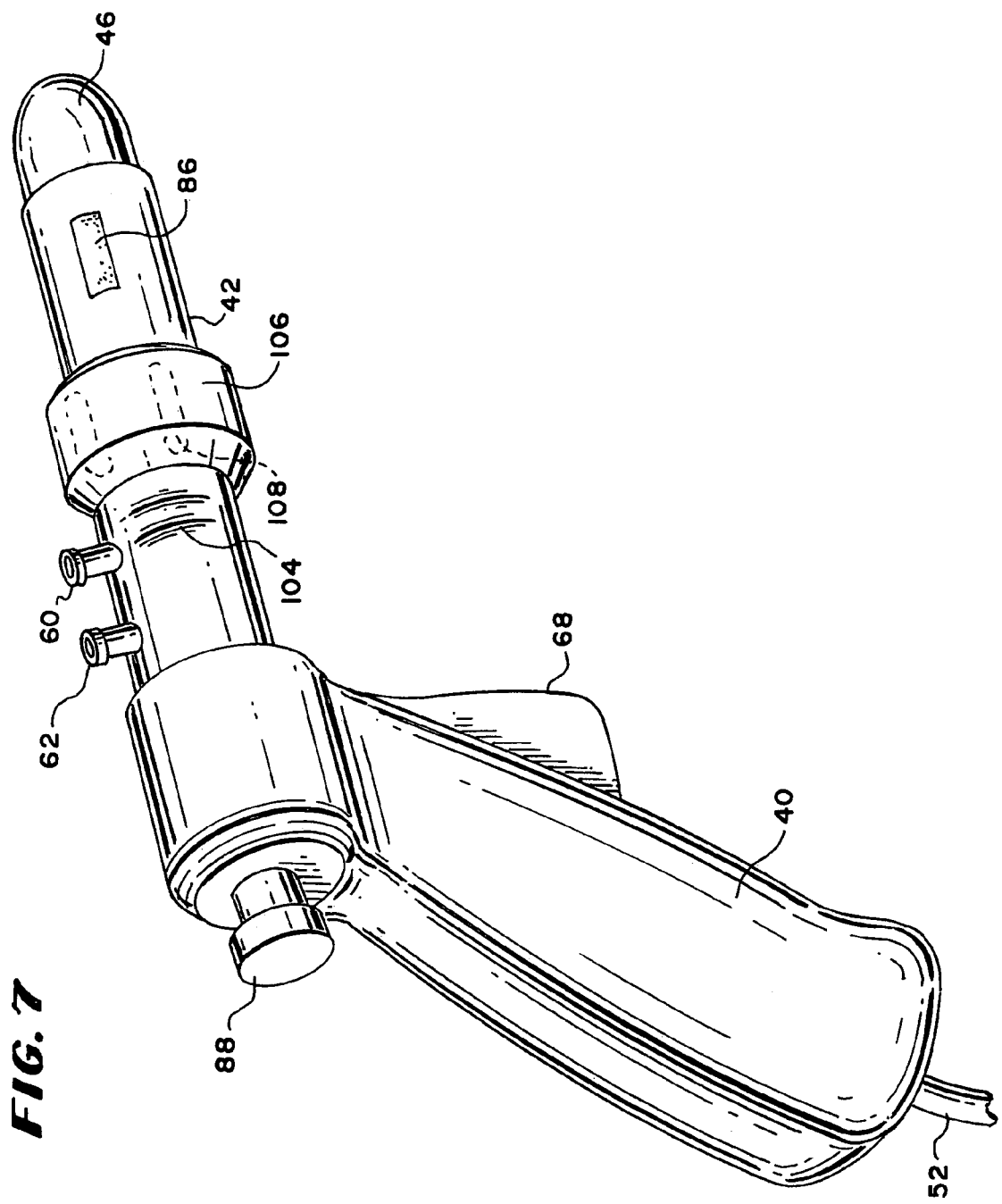
FIG. 7 is a perspective view of another treatment device usable in association with the system shown in FIG. 2, with straight energy application electrodes withdrawn for deployment.

In the embodiment shown in FIGS. 7 and 8, the barrel 42 includes a radially enlarged flange or ring 106, which has a greater outside diameter than the remainder of the barrel 42. The ring 106 includes a series of circumferentially spaced guide bores 108, through which the electrodes 66 pass for deployment. The guide bores 108 deploy the electrodes 66 in a generally straight orientation.

The push-pull control lever 66 extends the electrodes 66 (as shown in FIG. 8) and retracts the electrodes 66 (as shown in FIG. 7). The electrodes 66 move in a path that is generally parallel to the axis of the barrel 42.

In use (see FIG. 9), the physician guides the introducer 46 and barrel 42 into the anal canal 20 through the anal orifice 16, as before explained, while the electrodes 66 are maintained in their retracted position. The barrel 42 can include malleable sections 104 to allow the distal end 44 of the barrel 42 to be bent relative to the hand grip 40, either left or right, or up and down, or both, thereby aiding manipulation.

The physician can visualize the pectinate (dentate) line through the barrel 42, using, e.g., fiber optic 90, as also before explained. An ultrasound transmitter 74 on the barrel 42 can also be provided.

Figure 9A:
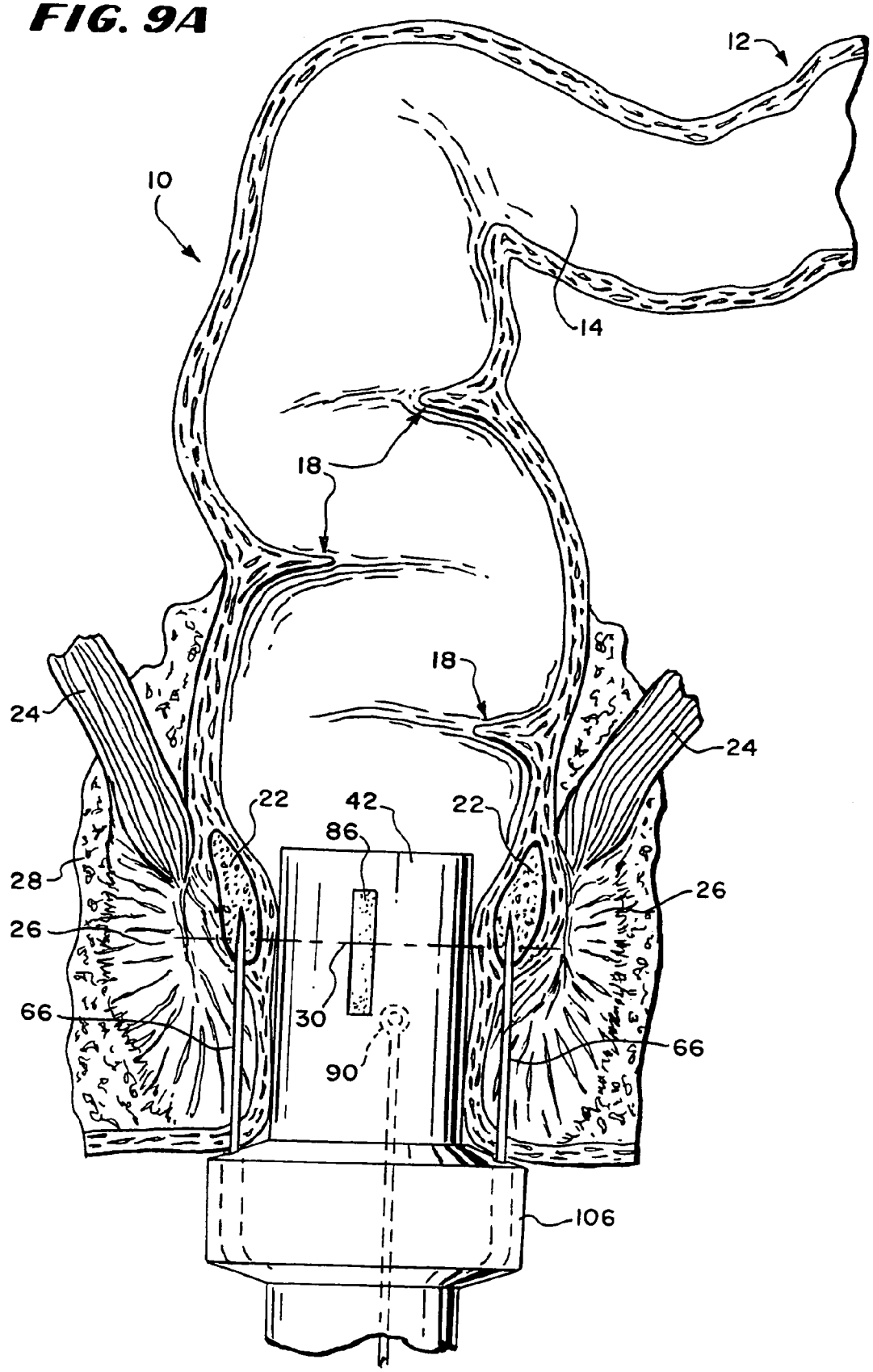
FIG. 9A is an anatomic view of the anal canal, with the treatment device shown in FIGS. 7 and 8 with the energy application electrodes extended into the internal sphincter muscle from outside the anal canal.

The barrel 42 enters the anal canal 20 for several centimeters, until the flange 106 contacts exterior tissue surrounding the anal orifice 16, as FIG. 9A shows. In this arrangement, the guide bores 108 become aligned in facing contact with the exterior tissue along the axis of the anal canal 20. The radially enlarged flange 106 also places the guide bores in axial alignment with the interior sphincter muscle 22. Depending upon the axial distance between the flange 106 and the pectinate (dentate) line 30, either sphincter muscle 22 or 26 or both sphincter muscles 22 and 26 can be placed in axial alignment with the guide bores 108.

Figure 9B:
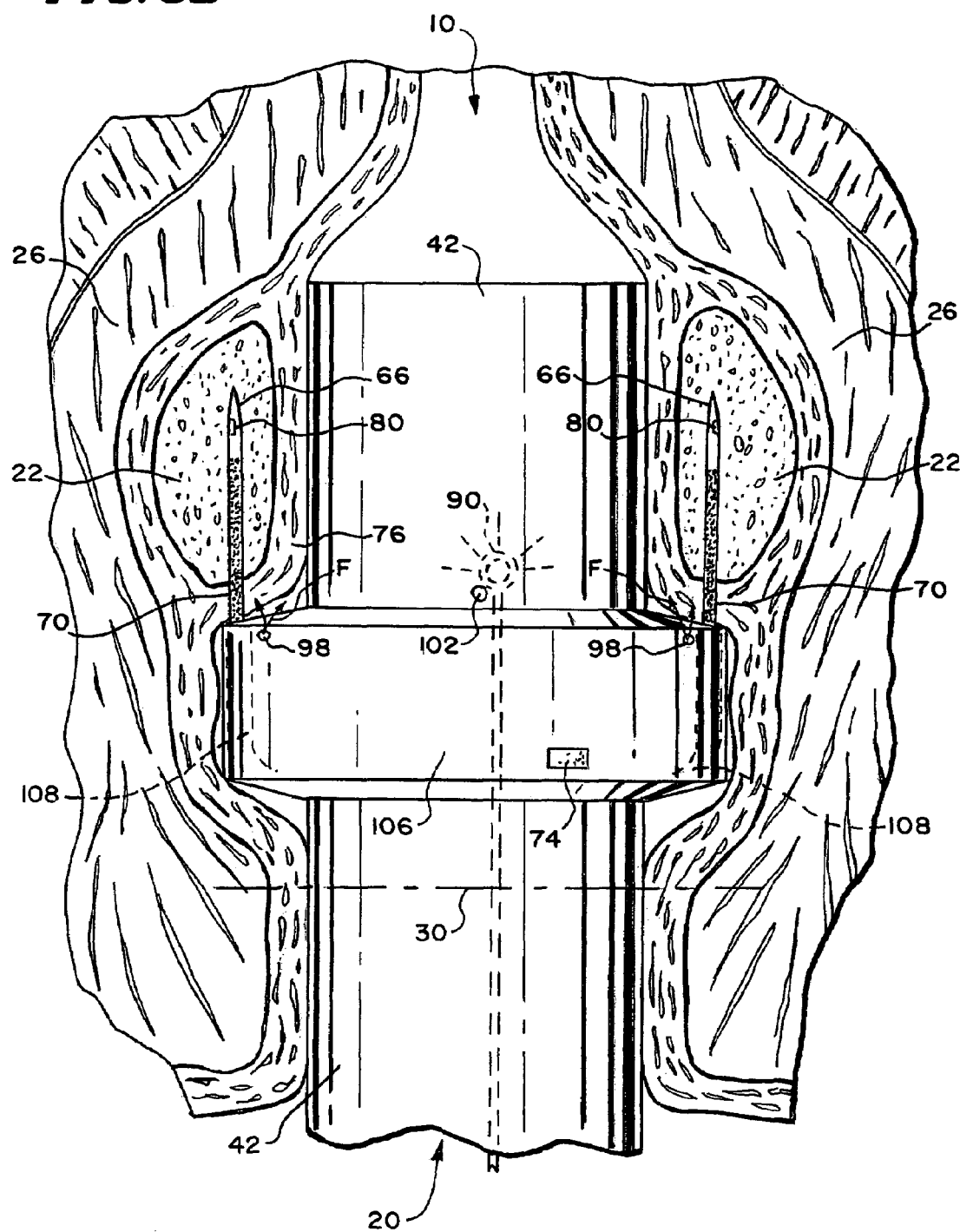
FIG. 9B is an anatomic view of the anal canal, with the treatment device shown in FIGS. 7 and 8 with the energy application electrodes extended into the internal sphincter muscle from inside the anal canal.

As FIG. 9B shows, the flange 106 can be sized to pass through the anal canal 20 into the rectum. The mucosal surface tissue 76 conforms about the radially enlarged diameter of the flange 106. In this arrangement, the guide bores 108 become aligned in facing contact with the mucosal tissue 76 along the axis of the anal canal 20. The radially enlarged flange also places the guide bores in axial alignment with the subsurface sphincter muscles 22 and 26. Depending upon the axial distance between the flange 106 and the pectinate (dentate) line 30, either sphincter muscle 22 or 26 or both sphincter muscles 22 and 26 can be placed in axial alignment with the guide bores 108.

Once the flange 106 is located at the desired location, the physician pulls rearward on the lever 68 to move the electrodes 66 into their extended position. The electrodes 66 travel longitudinally in an axial path aligned with axis of the anal canal 20. The straight electrodes 66 have distal sharpness and strength to penetrate a desired depth into one or both sphincter muscles 22 and 26. As previously described, an electrical insulating material 70 is coated about the proximal end of each electrode 66 to protect against damage to intermediate tissue 76.

FIGS. 9A and 9B show the exposed tips of the electrodes 66 contacting the internal sphincter muscle 22, as the external sphincter muscle 26 is typically not targeted for treatment. With the lever 68, however, the physician can control the depth of penetration to contact only the internal sphincter muscle 22 or just the external sphincter muscle 26.

The physician commands the controller 64 to apply radio frequency energy through the electrodes 66. The barrel 42 also preferably carries two temperature sensors 80, one to sense temperature conditions near the exposed distal end of the electrode 66, and the other to sense tissue surface temperature conditions. The controller 64 uses the sensed temperatures to control the application of radio frequency energy, as already described.

The flange 106 can also includes one or more lumens 98, situated close to each electrode 66. The fluid delivery apparatus 56 sprays processing fluid F through the lumen 98, to cool the tissue surface while energy is being applied by the electrode 66 to ohmically heat muscle beneath the surface. An aspiration lumen 102, coupled to the aspiration apparatus 58, removes fluid from the treatment site.

(iii) Tubular Electrode Device

Figure 18:
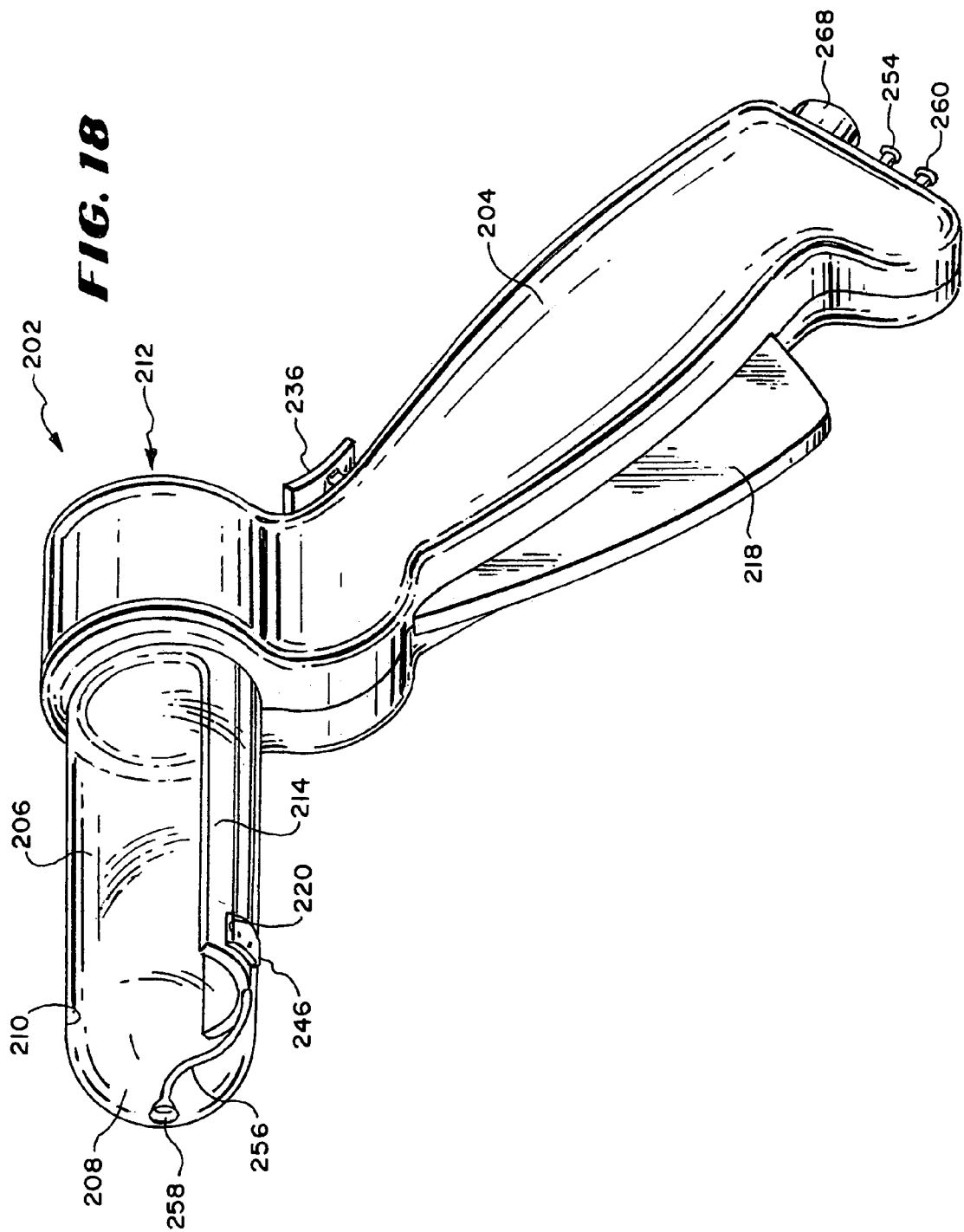
FIG. 18 is a perspective view of a hand manipulated device with a tubular barrel for deploying an array of needle electrodes in the anal cavity, the needle electrodes being shown in a retracted position.
Figure 19:
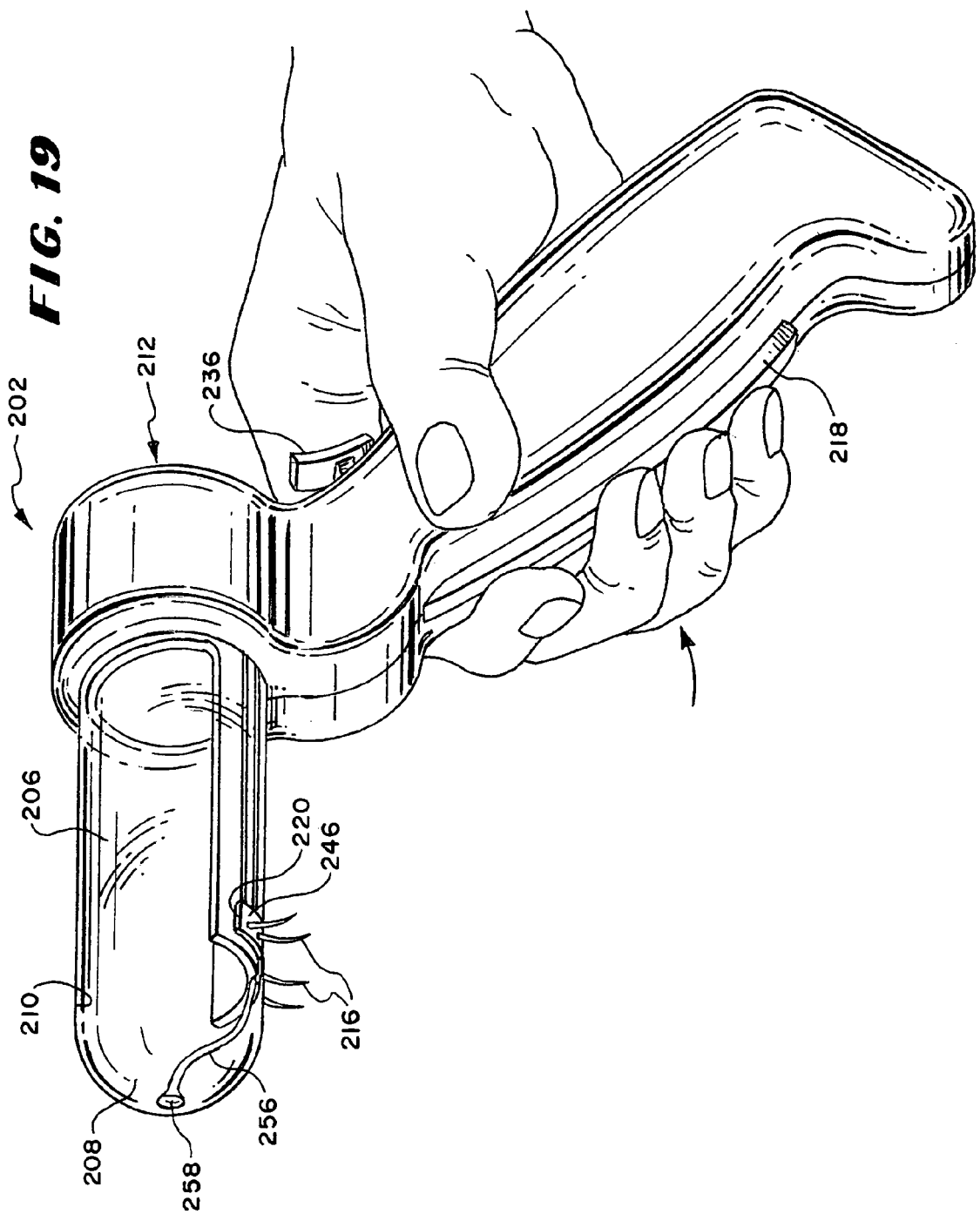
FIG. 19 is a perspective view of the hand manipulated device shown in FIG. 18, with the array of needle electrodes shown in their extended position.

FIGS. 18 and 19 show another hand manipulated device 202 for treating fecal incontinence. Like the device 36 shown in FIGS. 3 and 4, the device 200 includes a hand grip 204 made, e.g., from molded plastic. The hand grip 204 is sized to be conveniently grasped in the hand of a physician (as FIG. 19 shows).

The hand grip 204 carries a hollow, tubular barrel 206, which projects outward from the grip 204. The barrel 206 terminates with a blunt, rounded distal end 208. The rounded distal end 208 is configured to aid passage of the barrel 206 through the anal canal, without need for a separate introducer.

The barrel wall 210 is preferably made from a transparent, molded plastic material. In this arrangement, the hand grip 204 includes a viewing port 212 for looking into the hollow interior of the barrel 206. Looking through the view port 212 (see FIG. 25), the physician can visualize surrounding tissue through the transparent wall 210 of the barrel 206.

An electrode carrier 214 is mounted on the barrel wall 210 in the interior of the barrel 206. An array of needle electrodes 216 are movably contained in the carrier 214. The needle electrodes 216 are carried in the carrier 214 in a side-by-side relationship along an arcuate segment of the barrel 206. In the illustrated embodiment, the needle electrodes 216 occupy an arc of about 67.5 degrees on the barrel 206.

In the illustrated embodiment, the carrier 214 is mounted in the lower portion of the tubular barrel 206. Thus, when the barrel 206 is oriented horizontally, the needle electrodes 216 face downward, i.e., toward the ground. Of course, other orientations of the electrodes 216 in the barrel 206 are possible.

The needle electrodes 216 are mechanically linked to a finger-operated pull lever 218 on the hand grip 204. By operation of the pull lever 218, the distal ends of the needle electrodes 216 are moved between a retracted position within the carrier 214 (FIG. 18) and an extended position outside the carrier 214 (FIG. 19). In the extended position, the distal ends of the needle electrodes 216 project outwardly through slots 220 formed in the barrel wall 210.

The needle electrodes 216 can be linked in various ways to the pull lever 218. In the illustrated embodiment (see FIGS. 20 and 21), the proximal ends of the needle electrodes 216 are coupled to an annular shuttle element 222, which slides in a channel 224 in the viewing port 212. The center of the annular shuttle element 222 is open, so that visualization into the interior of the barrel 206 through the viewing port 212 is not obstructed.

Figure 20:
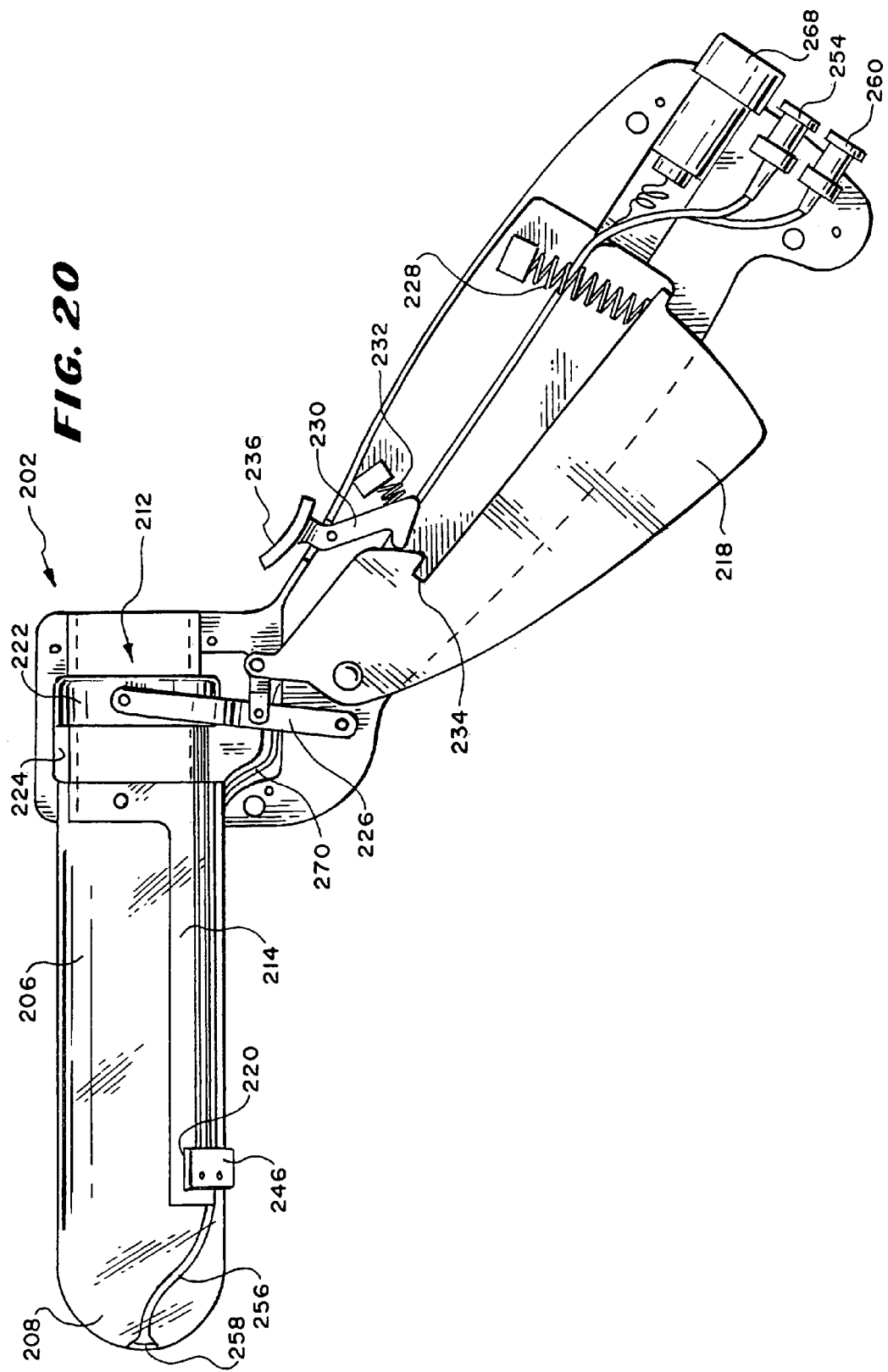
FIG. 20 is a side section view of the device shown in FIG. 18, showing the mechanism for deploying the array of needle electrodes, the needle electrodes being shown in their retracted position.

The annular shuttle element 222 is coupled by a pivot link 226 to the pull lever 218. A spring 228 normally biases the pull lever 218 toward a neutral position (see FIG. 20). In the neutral position, the pivot link 226 pulls the shuttle element 222 toward the rear of the channel 224 (i.e., away from the barrel 206). In this position, the distal ends of the needle electrodes 216 are withdrawn within the carrier 214. The spring 228 in the hand grip 204 thereby normally biases the needle electrodes 216 toward their retracted position (as FIG. 20 shows).

Figure 21:
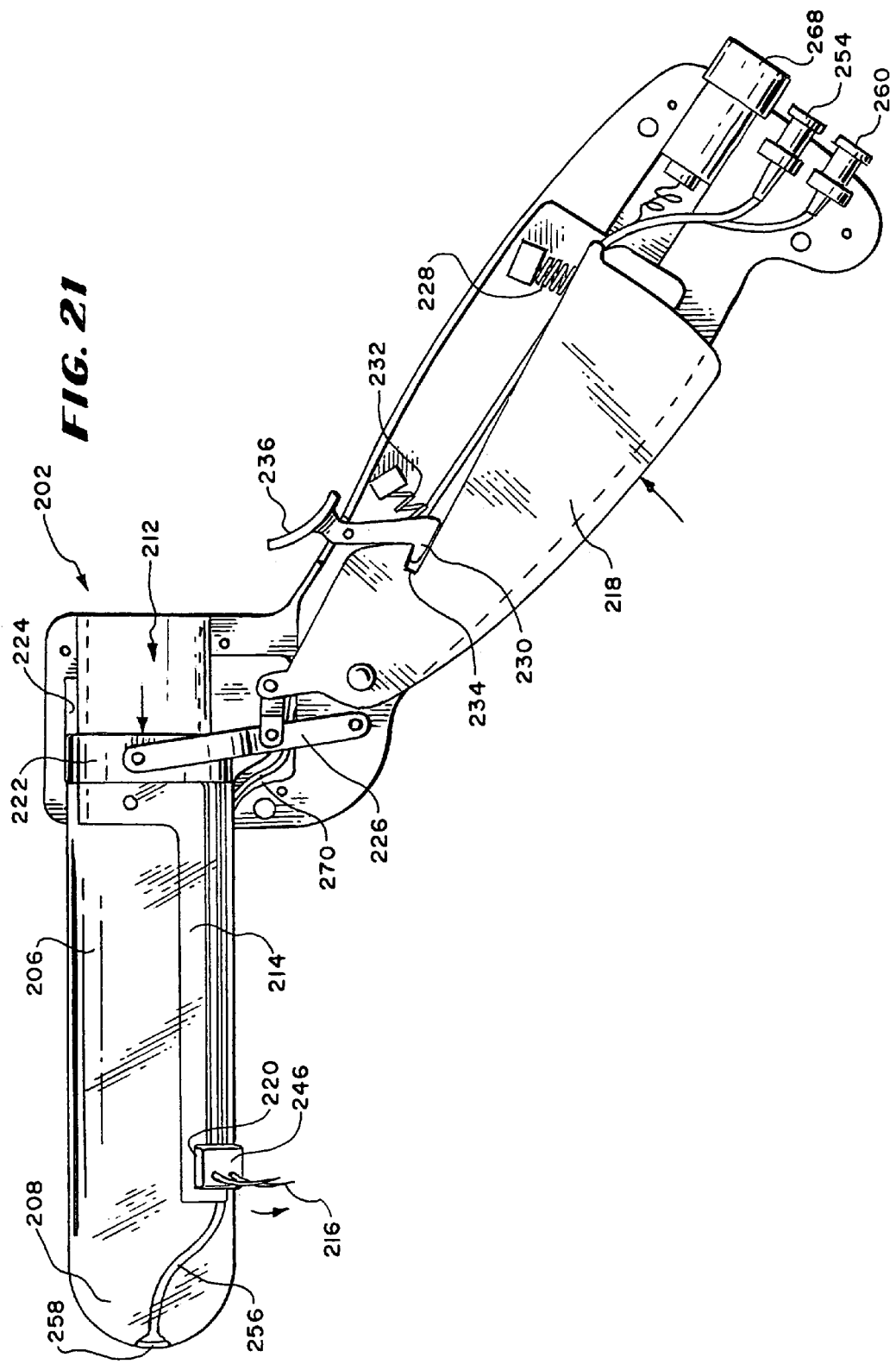
FIG. 21 is a side section view of the device shown in FIG. 18, showing the mechanism for deploying the array of needle electrodes, the needle electrodes being shown in their extended position.

As FIG. 21 shows, depressing the pull lever 218 against the force of the spring 228 pivots the link 226 to push the shuttle element 222 toward the front of the channel 224 (i.e., toward the barrel 206). The forward travel of the shuttle element 222 advances the needle electrodes 216 within the carrier 214, to cause the distal ends of the needle electrodes 216 to move into their extended positions through the barrel slots 220 (as FIG. 21 shows).

In the illustrated embodiment (best shown in FIGS. 20 and 21), a locking pawl 230 in the hand grip 204 is biased by a spring 232 to swing into an detent 234 in the pull lever 218 as the pull lever 218 is depressed. The spring-biased engagement of the pawl 230 within the detent 234 resists movement of the pull lever 218 out of the depressed position, thereby locking the needle electrodes 216 in their extended position.

The locking pawl 230 includes a release button 236, which projects outside the back of hand grip 204 (i.e., on the side opposite to the pull lever 218). Thumb pressure on the button 236 overcomes the biasing force of the spring 232 and frees the pawl 230 from the detent 234. The counter force of the spring 228 serves to urge the pull lever 218 toward the neutral position, thereby moving the needle electrodes 216 back to their normally retracted positions. There is therefore a spring-assisted return of the needle electrodes 216 into their normally retracted position.

In the illustrated embodiment (as FIGS. 22 and 23 best show), the carrier 214 comprises a molded plastic part with a preformed pattern of recesses forming channels, reservoirs, and mounts.

More particularly, the recesses form four electrode guide channels 238 in which the needle electrodes 216 slide. The channels 238 guide the sliding movement of the needle electrodes 216, which is occasioned by operation of the pull lever 218, as just described.

The distal ends of the needle electrodes 216 project beyond the guide channels 238 into other enlarged recesses, which form reservoirs 240. In the illustrated embodiment, there are two reservoirs 240, each accommodating the distal ends of two needle electrodes 216. A single continuous reservoir spanning across the carrier 214 could also be employed.

The carrier 214 can be mounted to the interior of the barrel 206 using, e.g., adhesive contained in cavities 242, or fasteners fitted within the cavities 242, or snap-fit or heat-staked posts fitted within the cavities 242. Once the carrier 214 is mounted, the reservoirs 240 register with the barrel slots 220, through which the distal ends of the needle electrodes 216 project when extended.

Figure 22:
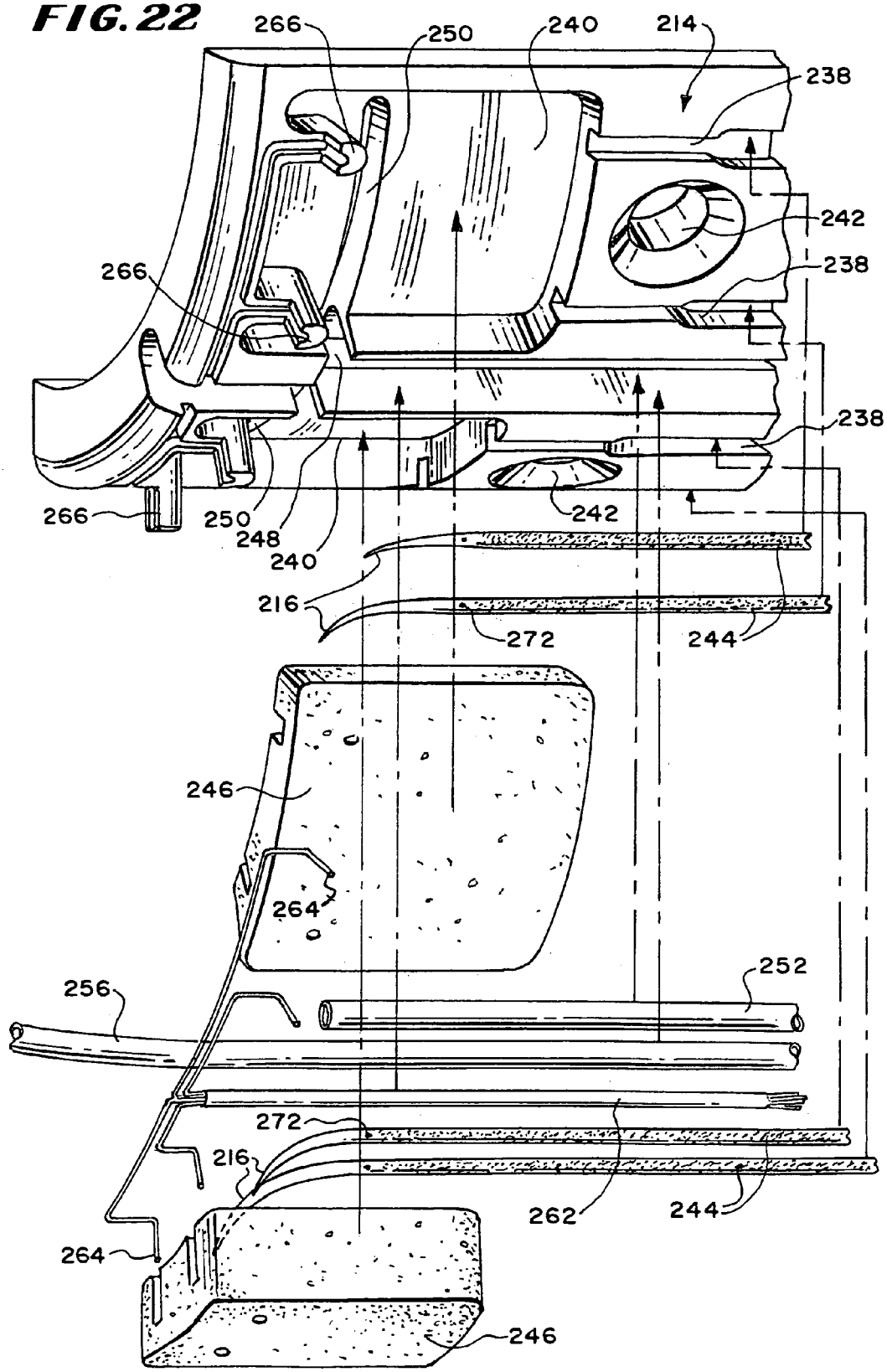
FIG. 22 is a perspective exploded view of the electrode-guiding carrier that is mounted in the tubular barrel of the device shown in FIG. 18.
Figure 23:
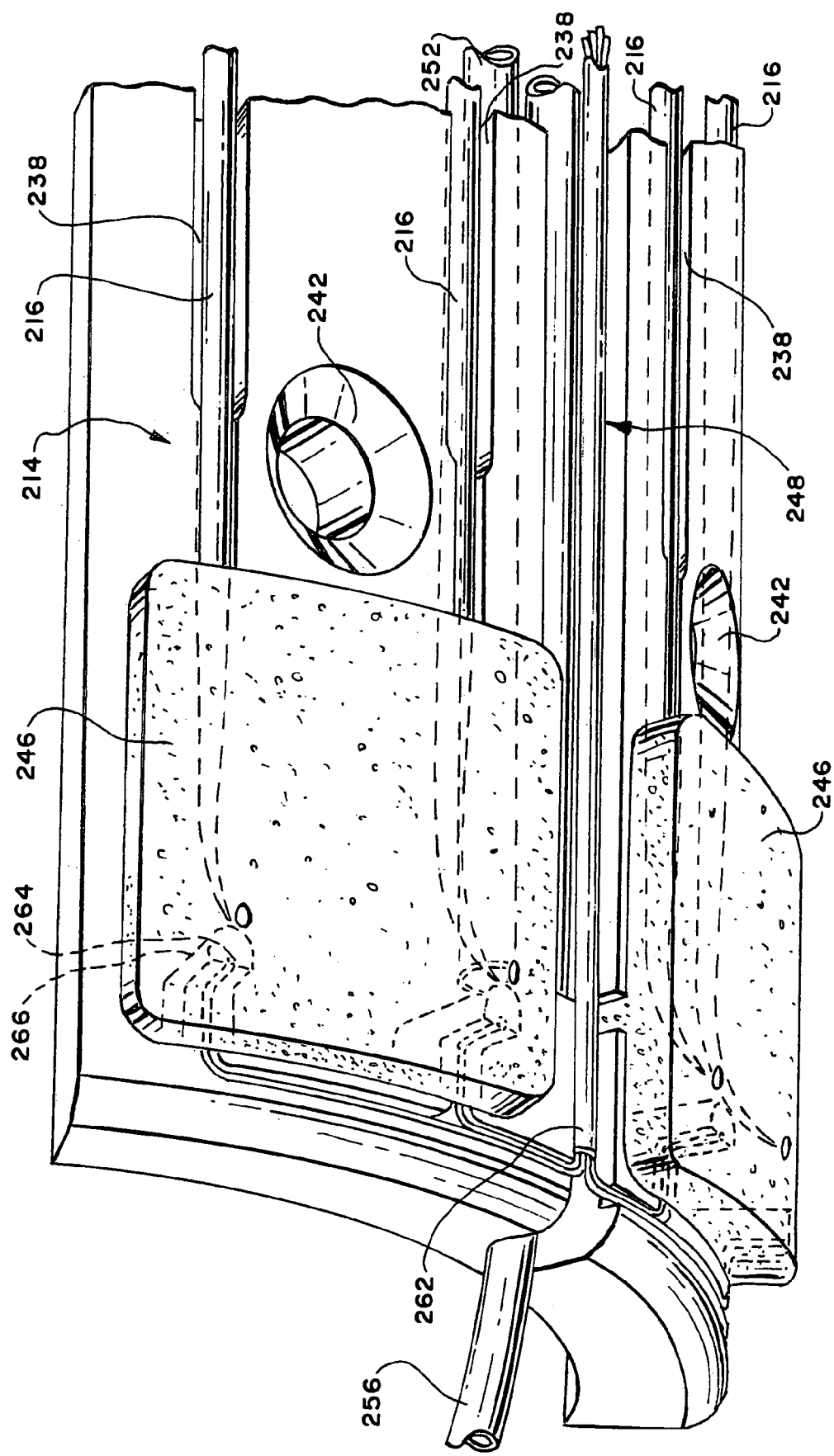
FIG. 23 is a perspective assembled view of the electrode-guiding carrier shown in FIG. 22.

As FIG. 22 shows, the distal ends of the needle electrodes 216 are normally biased with an antegrade bend, as previously described in connection with the FIG. 5 embodiment. Also as previously described, an electrical insulating material 244 is coated about the needle electrodes 216 (see FIG. 22), except for a prescribed region of the distal ends, where radio frequency energy is applied to tissue.

In the illustrated embodiment, electrode shields 246 overlay the reservoirs 240. The electrode shields 246 comprise a region of penetrable material, through which the electrodes can be advanced and retracted. The electrode shield material can include a closed cell structured material including semi-rigid foam insulation material, e.g., styrofoam material, polyethylene or urethane foam, neoprene, cork, rubber, soft plastic, or any number of comparable materials. Alternatively, the needle electrodes 216 can pass through formed apertures in the shields 246.

Another recess in the carrier 214 forms a utility channel 248, which extends between the reservoirs 240 generally in the middle of the carrier 214. The channel 248, at its distal end, communicates with branch manifolds 250 that extend into the reservoirs 240.

The channel carries tubing 252, the distal end of which terminates adjacent to the branch manifolds 250. The proximal end of the tubing 252 extends from the proximal end of the carrier 214, through the hand grip 204 (see FIG. 20), and is coupled to an exposed fitting 254 on the grip 204.

In use, the fitting 254 is intended to be coupled to the fluid delivery apparatus 56 (see FIG. 2). The apparatus 56 conveys a cooling liquid through the tubing 252, which is transferred by the manifold branches 250 into each reservoir 240.

In the illustrated embodiment, the electrode-penetrable material of the shields 246 can also be selected to be permeable to or to otherwise retain the cooling fluid introduced into the reservoirs 240. For example, the shield material can comprise an open cell material, such as open celled foam or another sponge-like, liquid retaining material. In this arrangement, cooling fluid conducted into each reservoir 240 permeates through the material of the overlaying electrode shield 246 to contact tissue. The liquid retaining material keeps cooling liquid in contact with mucosal tissue at a localized position surrounding the electrodes 216. By absorbing and retaining the flow of cooling liquid, the material also minimizes the aspiration requirements. The presence of the material to absorb and retain cooling liquid also reduces the flow rate and volume of cooling liquid required to cool mucosal tissue, and could eliminate the need for aspiration altogether.

Alternatively, separate ports for conducting cooling fluid can be provided in the electrode shields 246.

The utility channel 248 also carries another tubing 256, through which fluid can be aspirated. The distal end of the tubing 256 extends beyond the channel 248 (see FIG. 23) and is coupled to an aspiration port 258 in the distal end 208 of the barrel 206 (see FIG. 18). The proximal end of the tubing 256 extends from the carrier 214, through the hand grip 204 (see FIG. 20), and is coupled to an exposed fitting 260 on the grip 204. In use, the fitting 260 is intended to be coupled to the aspirating apparatus 58 (see FIG. 2).

Figure 29:
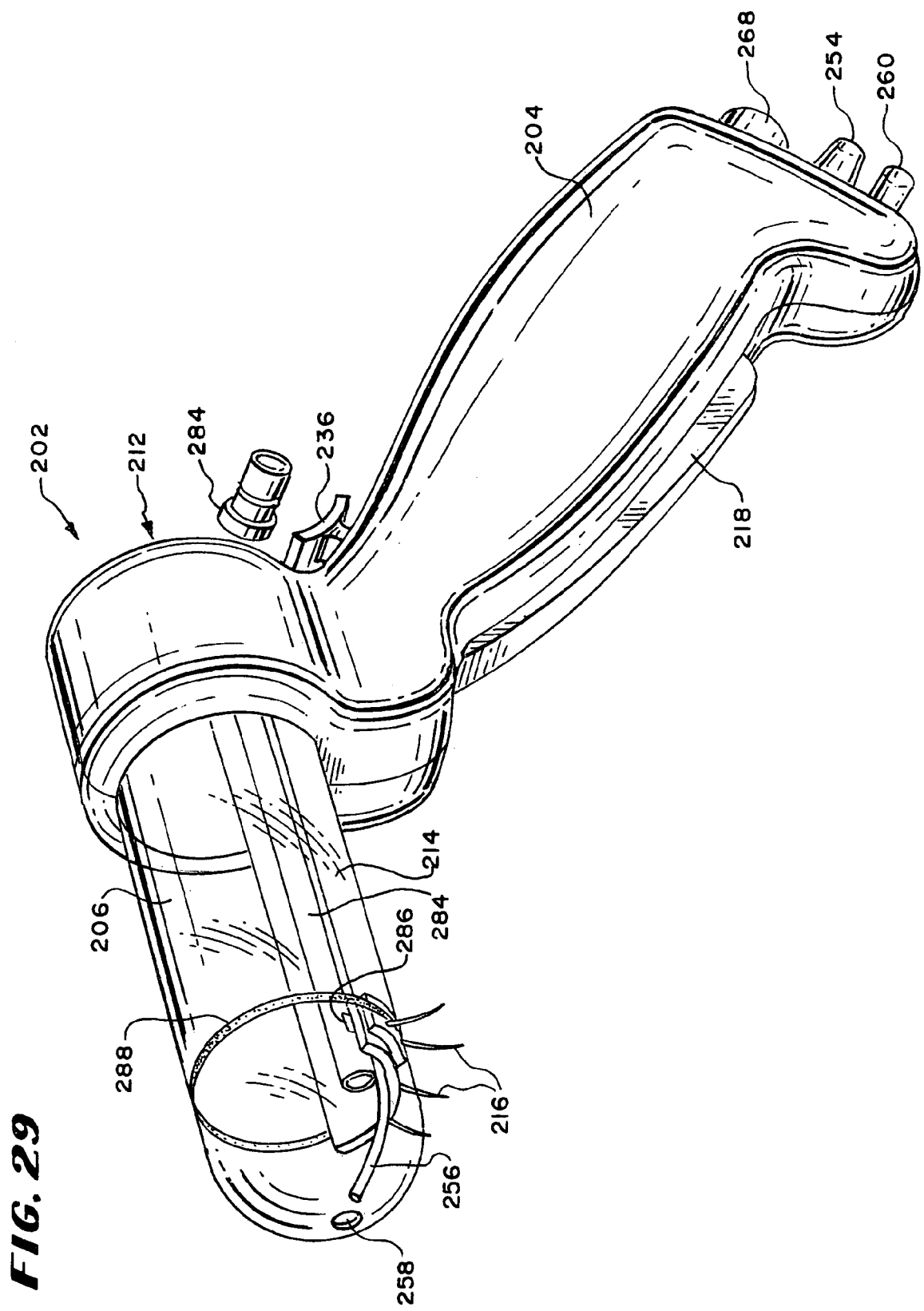
FIG. 29 is a perspective view of another embodiment of hand manipulated device with a tubular barrel for deploying an array of needle electrodes in the anal cavity, the needle electrodes being shown in an extended position.

Alternatively (as FIG. 29 shows), the distal end of the tubing 256 can terminate within the barrel 206 short of the port 258. In this arrangement, fluid that enters the barrel 206 through the port 258 is removed by aspiration through the tubing 256.

The utility channel 248 also carries cabling 262 that is coupled to temperature sensing devices 264. The devices 264 are attached to mounts 266 formed on the carrier 214, arranged such that one temperature sensor 264 is associated with each needle electrode 216. The sensors 264 sense tissue temperature conditions in the region adjacent to each needle electrode 216. The proximal end of the cabling 262 extends from the carrier 214, through the hand grip 204 (see FIG. 20), and is coupled to an exposed connector 268 on the grip 204.

Wires 270 (see FIG. 20) coupled to the needle electrodes 216 are also coupled to this connector 268. In use, the connector 268 is intended to be coupled to the generator 50. Preferably, the distal end of each needle electrode also carries a temperature sensor 272 (see FIG. 22). Wires for these temperature sensors are coupled to the connector 268 as well.

Figure 24:
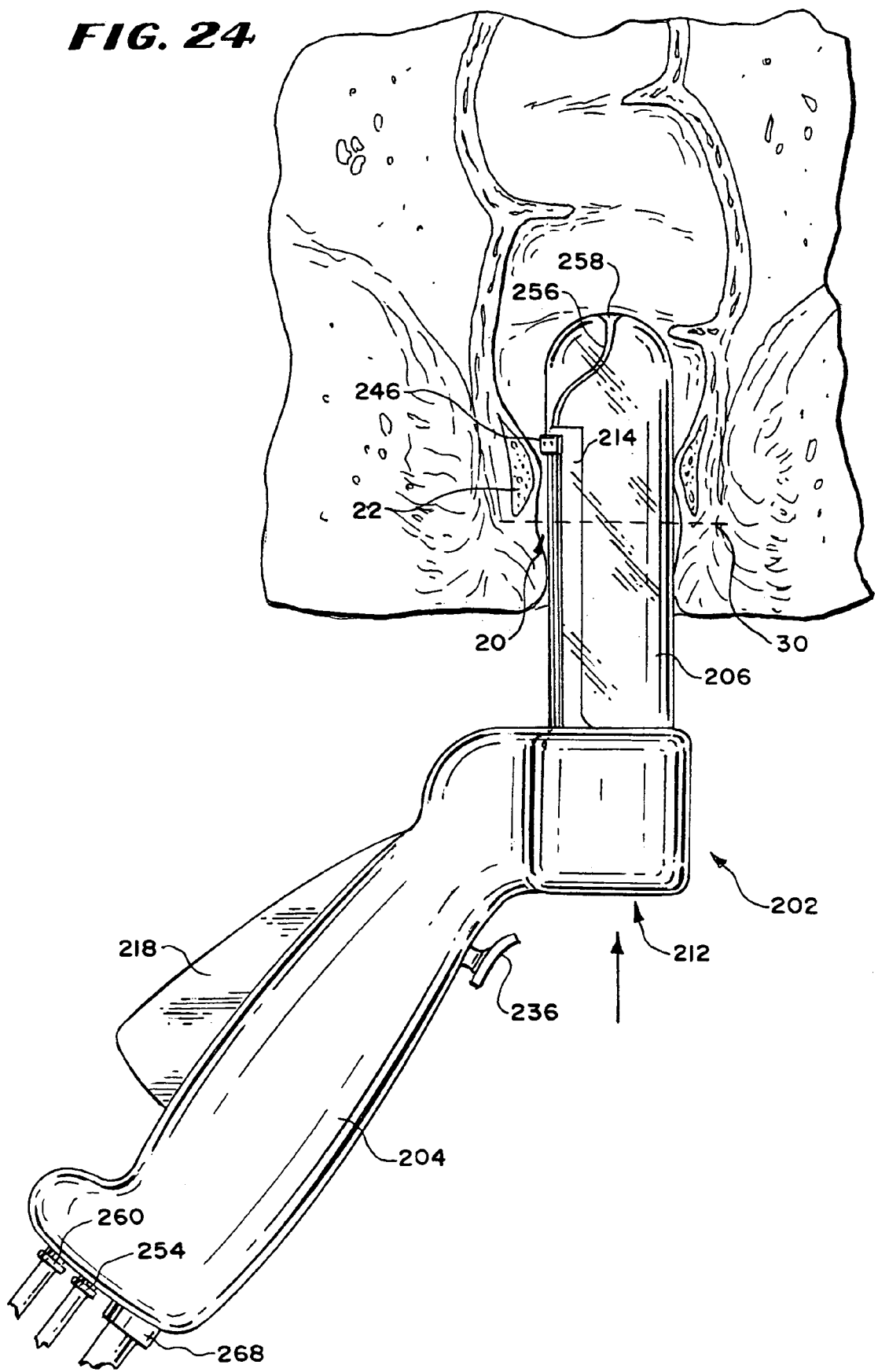
FIG. 24 is an anatomic view of the anal canal, with the treatment device shown in FIG. 18 inserted for positioning relative to the pectinate line with the needle electrodes in their retracted position.

In use (see FIG. 29), the physician grasps the hand grip 204 and guides the barrel 206 into the anal canal 20. The pull lever 218 is in the neutral position and not depressed, so the needle electrodes 216 occupy their normal retracted position (as FIG. 24 shows).

Looking through the viewing port 212 (see FIG. 25), the physician visualizes the pectinate (dentate) line 30 through the barrel 206. Looking through the barrel 206, the physician positions the distal ends of the needle electrodes 216 at a desired location above the pectinate (dentate) line 30. A fiberoptic can also be inserted into the barrel 206 to provide local illumination, or the physician can wear a headlamp for this purpose. In FIG. 29, a light pipe 284 comprising a plastic acrylic rod is inserted into the barrel 206 and removably secured in a retainer clip 286 in the barrel 206. The proximal end of the light pipe 284 is coupled via a cable (not shown) to an external high intensity light source (e.g., xenon).

As FIG. 29 also shows, the location of the distal ends of needle electrodes 216 can also be marked by an opaque band 288 printed, scribed, or pasted on the inside of the barrel 206. The band 288 visually aids the physician in aligning the electrodes 216 at the desired tissue location with respect to the dentate line 30.

Figure 25:
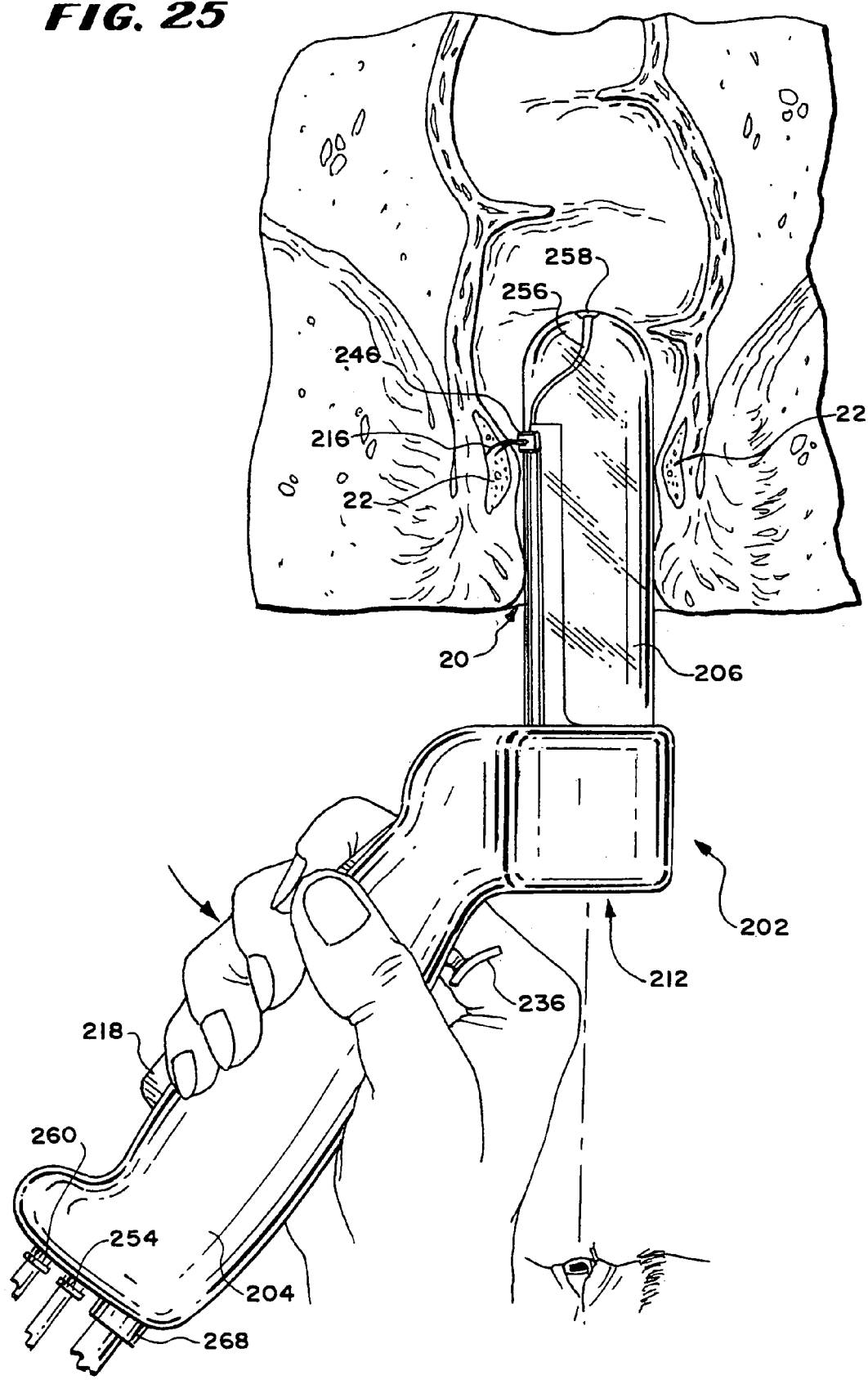
FIG. 25 is an anatomic view of the anal canal, with the treatment device shown in FIG. 18 inserted with the needle electrodes in their extended position inside the internal sphincter muscle.

Once the distal end of the barrel 206 is located at the targeted site, the physician depresses the pull lever 218 (see FIG. 25). The needle electrodes 216 advance to and lock in their extended positions. The distal ends of the electrodes 216 pierce and pass through the mucosal tissue into the muscle tissue of the target sphincter muscle. In FIG. 25, the distal end of the electrodes are shown penetrating the involuntary, internal sphincter muscle 22.

The physician commands the controller 64 to apply radio frequency energy through the needle electrodes 216. The energy can be applied simultaneously by all electrodes 216, or in any desired sequence.

As before described, the energy ohmically heats the muscle tissue. The controller 64 samples temperatures sensed by the sensors 264 and 272 to control the application of energy, to achieve tissue temperatures in the targeted muscle tissue in the range of 55° C. to 95° C.

The fluid delivery apparatus 56 conveys cooling fluid into the reservoirs 240 for discharge at the treatment site, to cool the mucosal surface while energy is being applied by the needle electrodes 216. The aspirating apparatus 58 draws aspirated material and the processing fluid through tubing 256 in the barrel 206 for discharge.

Figures 27, 28:
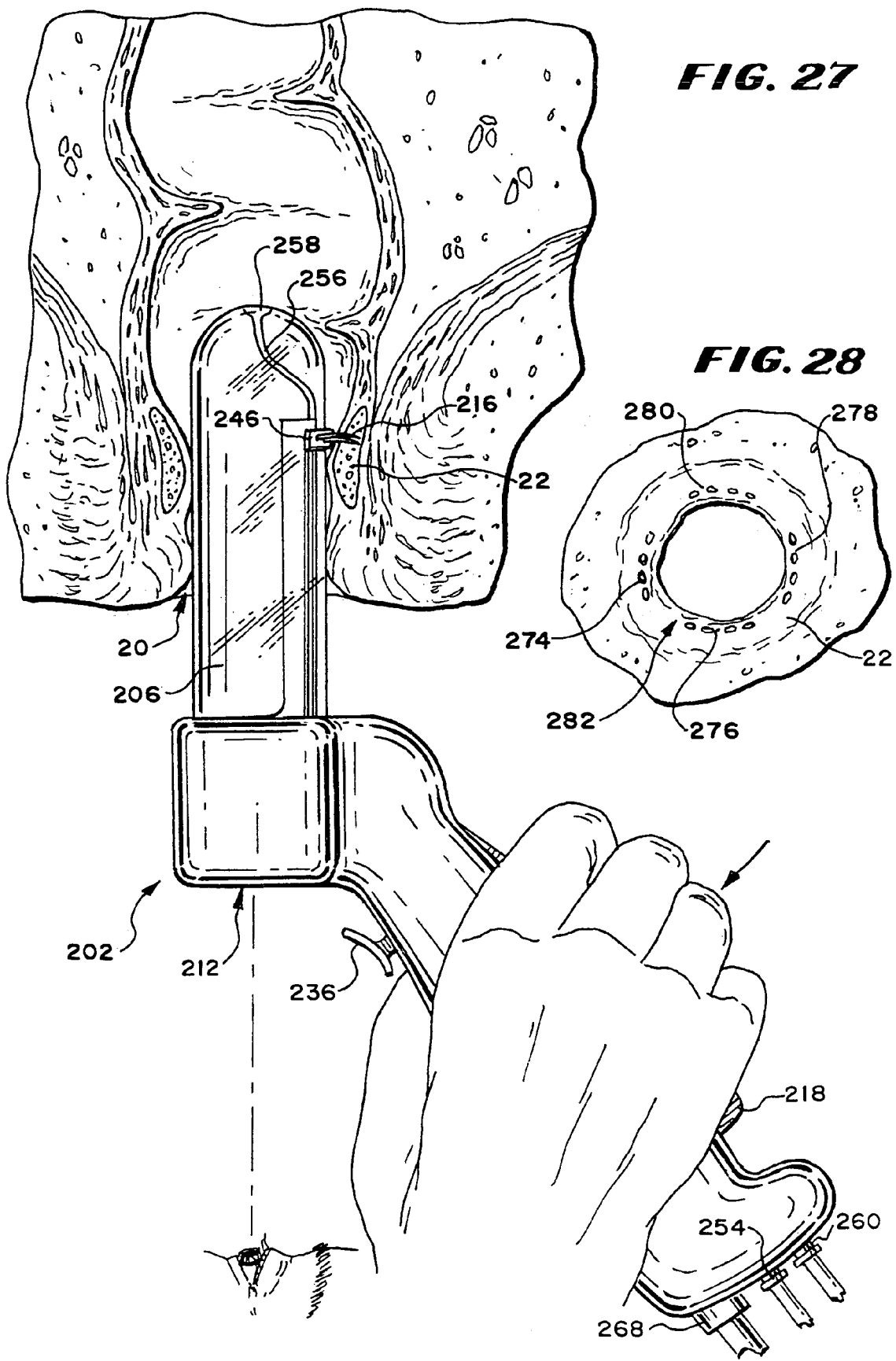
FIG. 27 is an anatomic view of the anal canal shown in FIG. 26, with the treatment device shown in FIG. 18 rotated to the new position and the needle electrodes in their extended position inside the internal sphincter muscle.
FIG. 28 is an anatomic view of a complex lesion pattern formed in the internal sphincter muscle by manipulating the device shown in FIG. 18 in the manner shown in FIGS. 24 to 27.

The array of needle electrodes 216 creates a first pattern of multiple lesions 274, as FIG. 28 shows.

Upon the satisfactory creation of the first lesion pattern 274, as just described, the physician actuates the button 236 to release the locking pawl 230 from the detent 234 (as previously described and shown in FIGS. 20 and 21). The pull lever 218 returns to the spring-biased neutral position, thereby moving the needle electrodes 216 back to their retracted positions.

Figure 26:
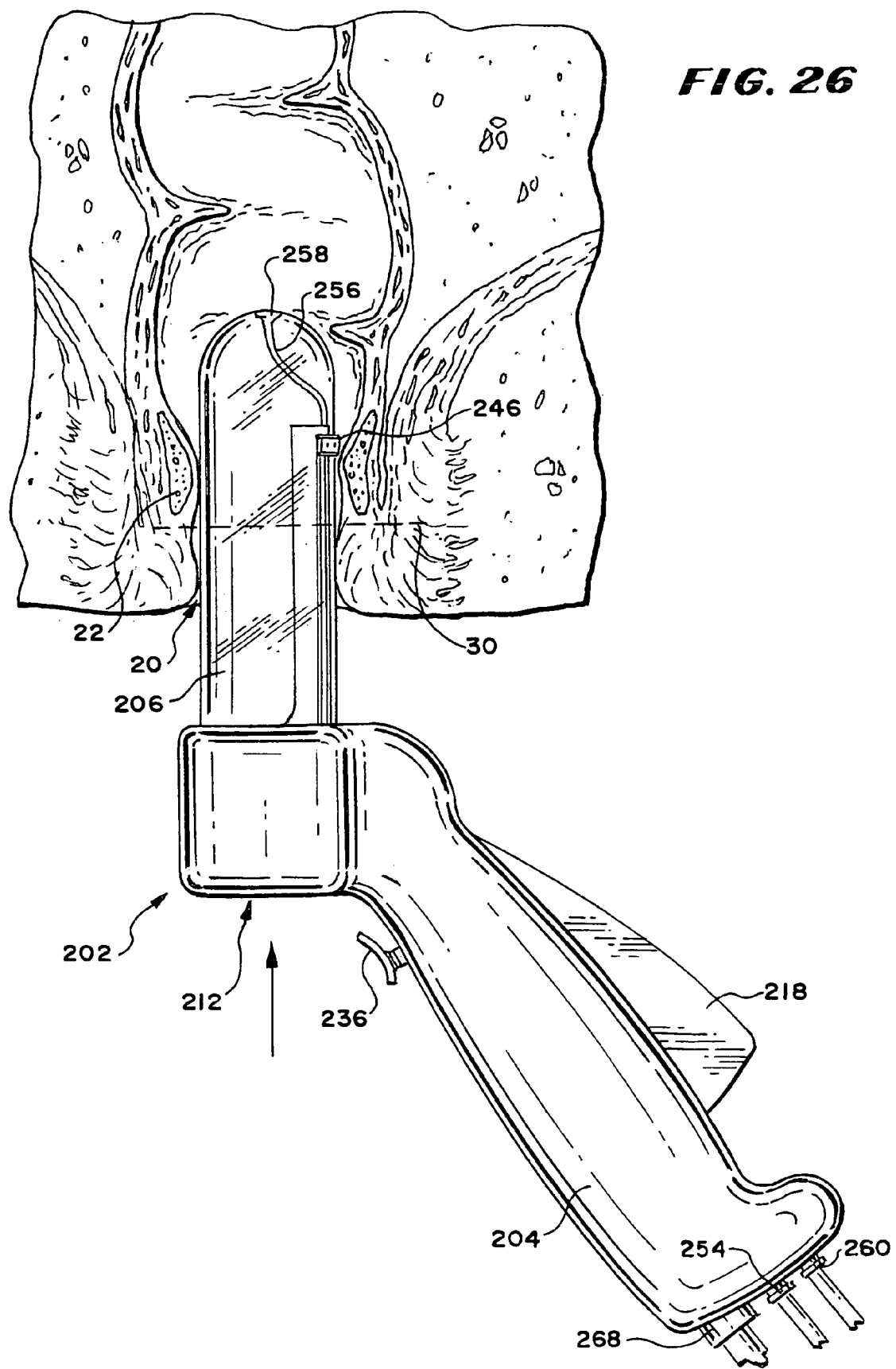
FIG. 26 is an anatomic view of the anal canal shown in FIGS. 24 and 25, with the treatment device shown in FIG. 18 rotated to a new position and the needle electrodes in their retracted position.

Still grasping the hand grip 204 and visualizing through the viewing port 212, the physician rotates the barrel 206 a selected arcuate distance from its first position (see FIG. 26), maintaining the desired location above the pectinate (dentate) line 30. For example, the physician can rotate the barrel 206 by ninety degrees.

The physician again deploys the needle electrodes 216 and performs another lesion generating sequence (see FIG. 27). A second lesion pattern 276 is created (see FIG. 28), circumferentially spaced ninety degrees from the first lesion pattern 274.

The physician repeats the above described sequence two additional times, rotating the barrel 206 at successive intervals, e.g., ninety degrees each. Third and fourth lesion patterns 278 and 280 are thereby created (see FIG. 28), each circumferentially spaced apart by ninety degree intervals. This protocol forms a composite lesion pattern 282 (see FIG. 28), which provides a density of lesions in the targeted sphincter tissue region to provoke a desired contraction of the sphincter tissue.

III. Alternative Treatment Devices for Treating Fecal Incontinence

A. Carrier and Introducer Assembly

Figure 10:
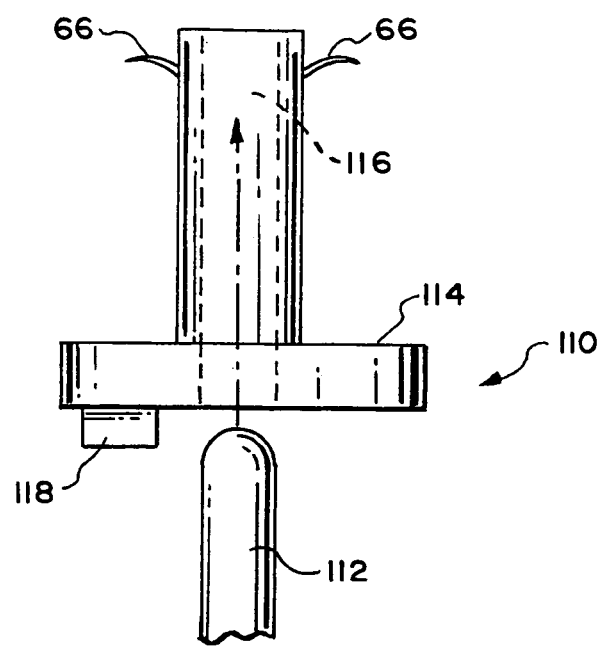
FIG. 10 is a side elevation view of a two part treatment device usable in association with the system shown in FIG. 2, with energy application electrodes extended for use in a radial direction.
Figure 11:
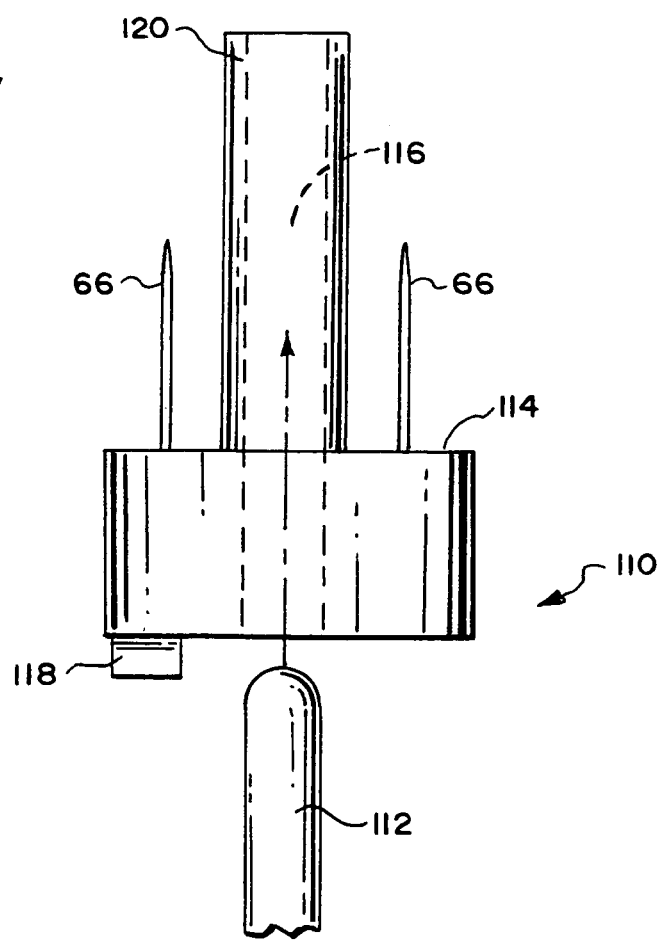
FIG. 11 is a side elevation view of a two part treatment device usable in association with the system shown in FIG. 2, with straight energy application electrodes extended for use in an axial direction.

FIGS. 10 and 11 show an alternative embodiment for a treatment device 110. In this embodiment, the treatment device 110 comprises two component parts: a blunt tip introducer 112 and an electrode carrier 114. The introducer 112 is sized for insertion into the anal canal 20 through the anal orifice 16, like the introducer 46 described in the preceding embodiments. The electrode carrier 114 includes an interior bore 116 that is sized to enable the carrier 114 to be advanced over the introducer 112 into the anal canal 20.

The carrier 114 is preferably made of a material to enable the physician to visualize the location of the pectinate (dentate) line 30, e.g., by direct visualization through the carrier 114. The carrier 114 can be made from a transparent material, e.g., clear plastic, for this purpose. Alternatively, the carrier 114 can include slots, which open a viewing field. The carrier 114 carries an array of electrodes 66, as previously described, which can either be bent (as FIG. 10 shows) or straight (as FIG. 11 shows). An actuator 118 on the carrier 114 moves the electrodes 66 between retracted and extended positions, as also previously describes.

Figure 12:
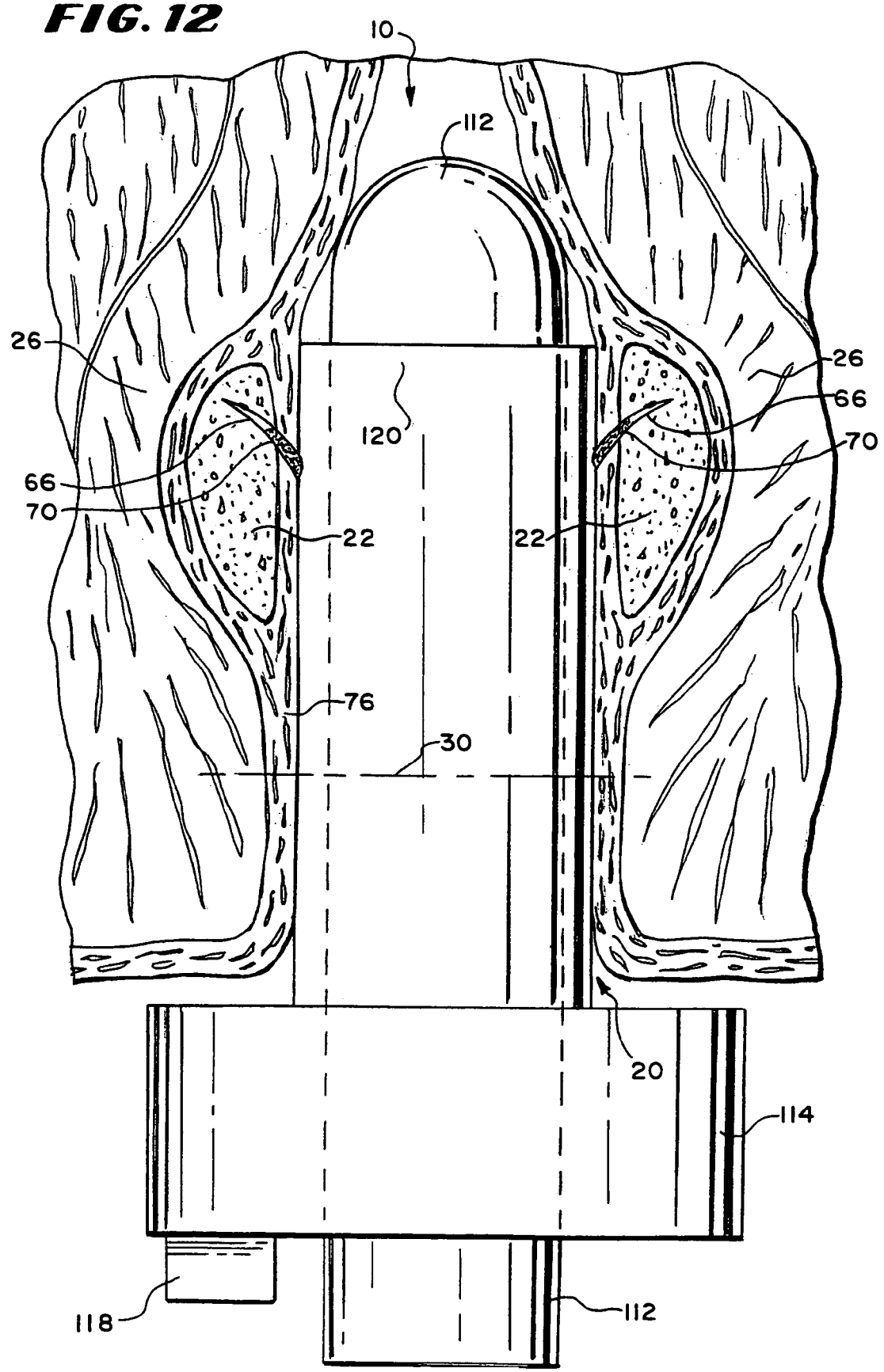
FIG. 12 is an anatomic view of the anal canal, with the treatment device shown in FIG. 11, with the energy application electrodes extended radially into the internal sphincter muscle.

In use (see FIG. 12), the physician manipulates the introducer 112 to guide it into the anal canal 20 through the anal orifice 16. The physician then advances the electrode carrier 114 over the introducer 112, until its distal end 120 is aligned at the targeted site. The physician removes the introducer 112 and operates the actuator 118 to move the electrodes 66 into their extended position. The electrodes 66 pierce and pass through the mucosal tissue 76 into the muscle tissue of the target sphincter muscle, as previously described.

The physician commands the controller 64 to apply radio frequency energy through the electrodes 66, to ohmically heat the muscle tissue. The electrodes 66 carry insulation material 70 about their proximal ends to prevent surface mucosal damage while subsurface ohmic heating occurs.

In this arrangement, as before described with respect to the previous embodiments, the electrodes 66 can carry temperature sensors 80, by which the controller 64 samples temperatures to control the application of energy. Cooling fluid can also be conveyed through lumen the electrode carrier 114, as also previously described.

B. Expandable Structures

Figure 13:
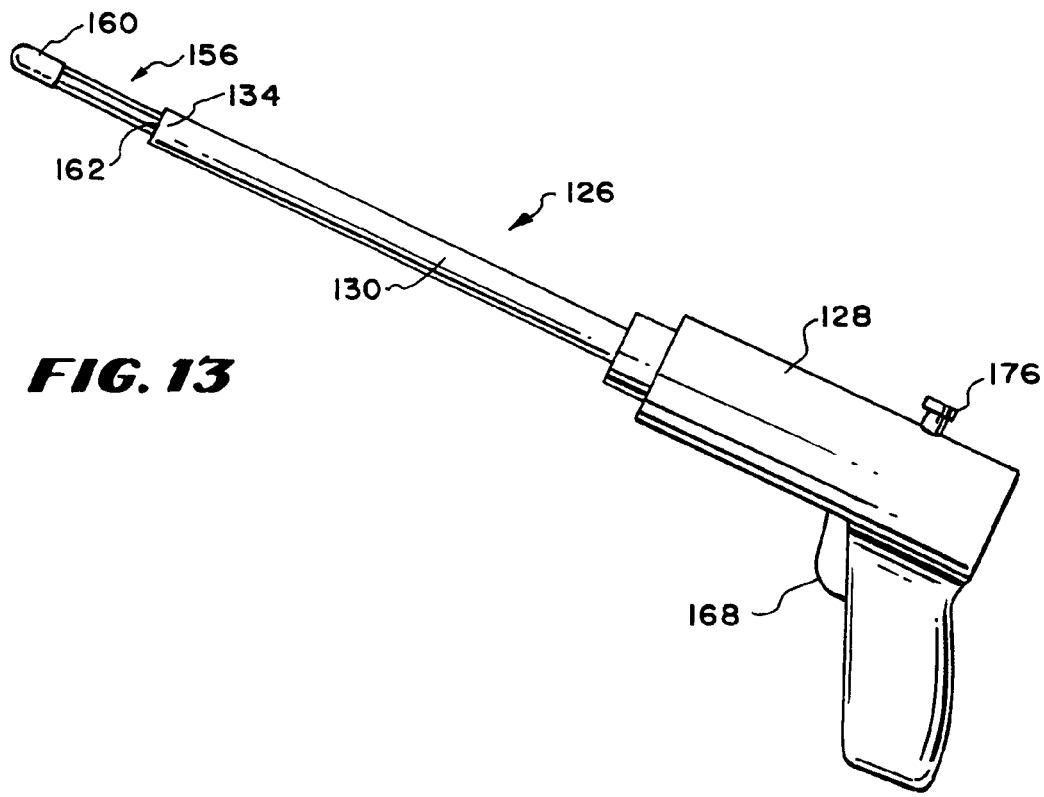
FIG. 13 is a perspective view of another treatment device usable in association with the system shown in FIG. 2, with an expandable structure that carries energy application electrodes for deployment, the structure being shown in a collapsed condition.
Figure 14:
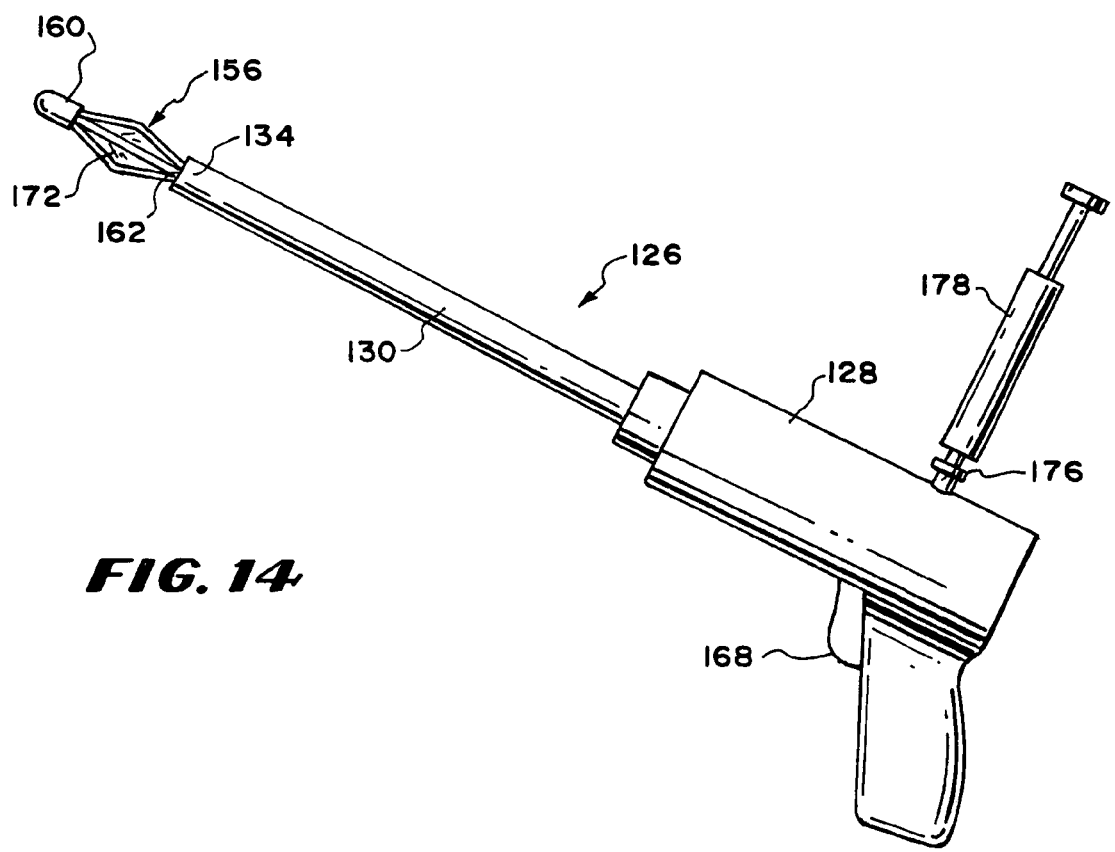
FIG. 14 is a perspective view of the treatment device shown in FIG. 13, with the structure expanded.

FIGS. 13 and 14 show another alternative embodiment for a treatment device 126. The device 126 includes a handle 128 made, e.g., from molded plastic. The handle 128 carries a flexible catheter tube 130. The catheter tube 130 can be constructed, for example, using standard flexible, medical grade plastic materials, like vinyl, nylon, poly(ethylene), ionomer, poly(urethane), poly(amide), and poly(ethylene terephthalate). The handle 128 is sized to be conveniently held by a physician, to introduce the catheter tube 130 into the anal canal 20.

The handle 128 and the catheter tube 130 can form an integrated construction intended for a single use and subsequent disposal as a unit. Alternatively, the handle 128 can comprise a nondisposable component intended for multiple uses. In this arrangement, the catheter tube 130, and components carried at the end of the catheter tube 130 (as will be described), comprise a disposable assembly, which the physician releasably connects to the handle 128 at time of use and disconnects and discards after use. The catheter tube 130 can, for example, include a male plug connector that couples to a female plug receptacle on the handle 128.

Figure 15:
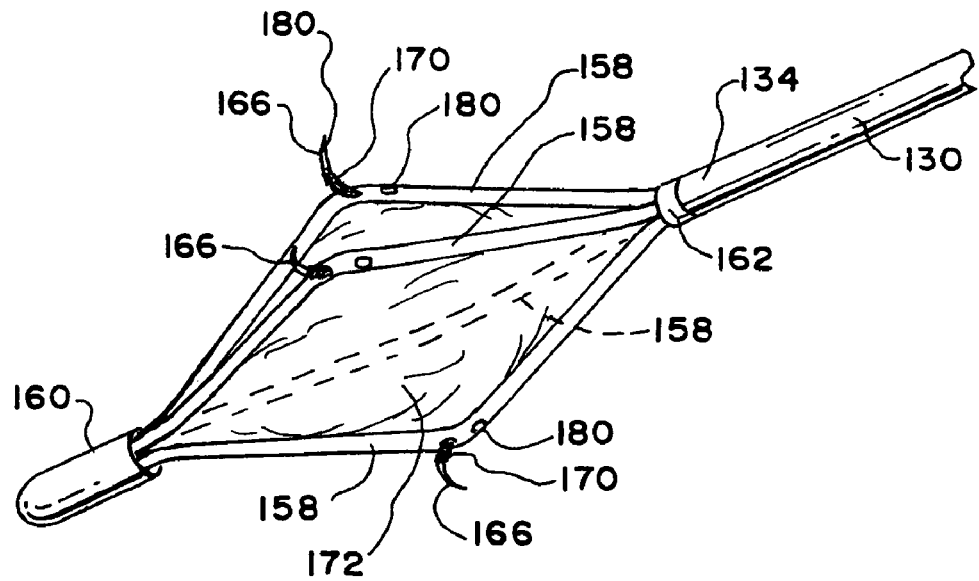
FIG. 15 is an enlarged perspective view of an expandable structure carrying four electrodes, which is useable in association with the treatment device shown in FIG. 13, showing the structure expanded and the four electrodes extended for use.
Figure 16:
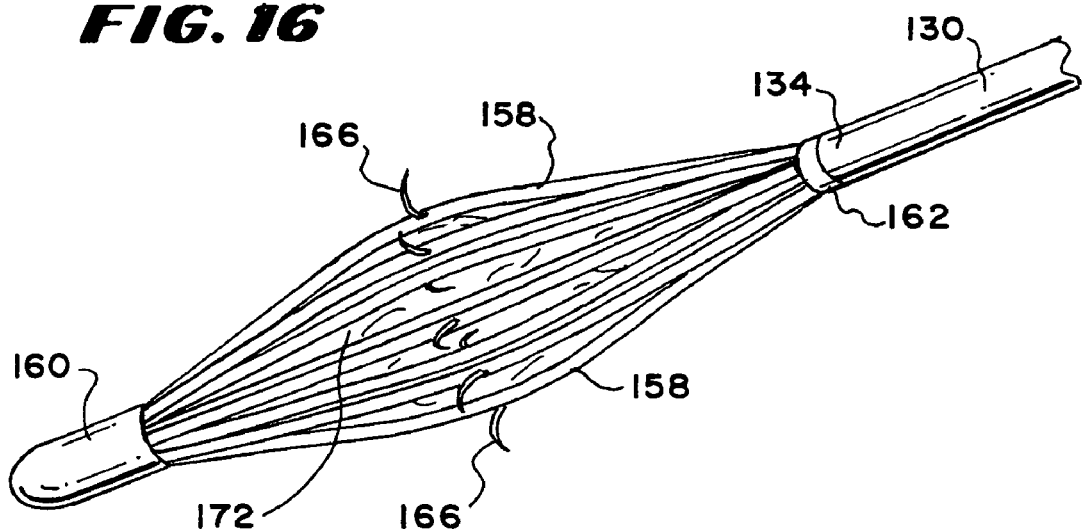
FIG. 16 is an enlarged perspective view of an expandable structure carrying eight electrodes, which is useable in association with the treatment device shown in FIG. 13, showing the structure expanded and the eight electrodes extended for use.

The catheter tube 130 has a distal end 134, which carries a three-dimensional basket 156. The basket 156 includes one or more spines 158 (see FIGS. 15 and 16), and typically includes from four to eight spines 158, which are assembled together by a distal hub 160 and a proximal base 162. FIG. 15 shows a typical basket comprising four spines 158. FIG. 16 shows a typical basket comprising eight spines 158.

As FIGS. 15 and 16 best show, the distal hub 160 presents a blunt distal surface. The hub 160 thereby serves as an introducer, to aid passage of the device 126 through the anal canal.

Each spine 158 preferably comprises a flexible tubular body made, e.g. from molded plastic, stainless steel, or nickel titanium alloy. The cross sectional shape of the spines 158 can vary, possessing, e.g., a circular, elliptical, square, or rectilinear shape.

In the embodiments shown in FIGS. 13 to 16, an expandable structure 172 comprising a balloon is located within the basket 156. The balloon structure 172 can be made, e.g., from a Polyethylene Terephthalate (PET) material, or a polyamide (non-compliant) material, or a radiation cross-linked polyethylene (semi-compliant) material, or a latex material, or a silicone material, or a C-Flex (highly compliant) material. Non-compliant materials offer the advantages of a predictable size and pressure feedback when inflated in contact with tissue. Compliant materials offer the advantages of variable sizes and shape conformance to adjacent tissue geometries.

The balloon structure 172 presents a normally, generally collapsed condition, as FIG. 13 shows. In this condition, the basket 156 is also normally collapsed about the balloon structure 172, presenting a low profile for deployment through the anal canal 20.

The catheter tube 130 includes an interior lumen, which communicates with the interior of the balloon structure 172. A fitting 176 (e.g., a syringe-activated check valve) is carried by the handle 128. The fitting 176 communicates with the lumen. The fitting 176 couples the lumen to a syringe 178 (see FIG. 14). The syringe 178 injects fluid under pressure through the lumen into the balloon structure 172, causing its expansion.

Expansion of the balloon structure 172 urges the basket 156 to open and expand (as FIGS. 14 to 16 show). The force exerted by the balloon structure 172, when expanded, is sufficient to exert force upon the tissue surrounding the basket 156.

As FIGS. 15 and 16 show, each spine 158 carries an electrode 166. Each electrode 166 is carried within the tubular spine 158 for sliding movement. Each electrode 166 slides from a retracted position, withdrawn in the spine 158 (shown in FIGS. 13 and 14), and an extended position, extending outward from the spine 158 (shown in FIGS. 15 and 16) through a hole in the spine 158.

A push-pull lever 168 on the handle 128 is coupled by one or more interior wires to the sliding electrodes 166. The lever 168 controls movement electrodes between the retracted position (by pulling rearward on the lever 168) and the extended position (by pushing forward on the lever 168).

The electrodes 166 can be formed from various energy transmitting materials. In the illustrated embodiment, the electrodes 166 are formed from nickel titanium. The electrodes 166 can also be formed from stainless steel, e.g., 304 stainless steel, or a combination of nickel titanium and stainless steel. The electrodes 166 have sufficient distal sharpness and strength to penetrate a desired depth into targeted muscle tissue in the rectum.

To further facilitate penetration and anchoring in the targeted muscle tissue, each electrode 166 is preferably biased with a bend. Movement of the electrode 166 into the spine 158 overcomes the bias and straightens the electrode 166.

In the illustrated embodiment (see FIGS. 15 and 16), each electrode 166 is normally biased with an antegrade bend (i.e., bending toward the proximal base 162 of the basket 156). Alternatively, each electrode 166 can be normally biased toward an opposite retrograde bend (i.e., bending toward the distal hub 160 of the basket 158).

As FIG. 15 shows, an electrical insulating material 170 is coated about the proximal end of each electrode 166, as described in the preceding embodiments. When the distal end of the electrode 166 penetrating the target muscle tissue of the rectum transmits radio frequency energy, the material 170 insulates the mucosal surface of the rectum from direct exposure to the radio frequency energy. Thermal damage to the mucosal surface is thereby avoided. As previously described, the mucosal surface can also be actively cooled through holes in the spines 158 during application of radio frequency energy, to further protect the mucosal surface from thermal damage.

Of course, a greater or lesser number of spines 158 and/or electrodes 166 can be present, and the geometric array of the spines 158 and electrodes 166 can vary.

In the illustrated embodiment (see FIG. 15), two temperature sensors 180 are provided, one to sense temperature conditions near the exposed distal end of the electrode 166, and the other to sense temperature conditions in the insulated material 170. Preferably, the second temperature sensor 180 is located on the corresponding spine 158, which rests against the mucosal surface when the balloon structure 72 is inflated.

In use (see FIG. 17), the physician manipulates an anuscope 200 into the anal canal 20 through the anal orifice 16. The physician then advances the catheter tube 130 and basket 156 through the anuscope 200, with the basket 156 in its collapsed condition. The physician visualizes the location of the basket 156 through the anuscope, to place the basket 156 at the targeted site. Ultrasonic visualization can also be employed, as previously described.

Figure 17:
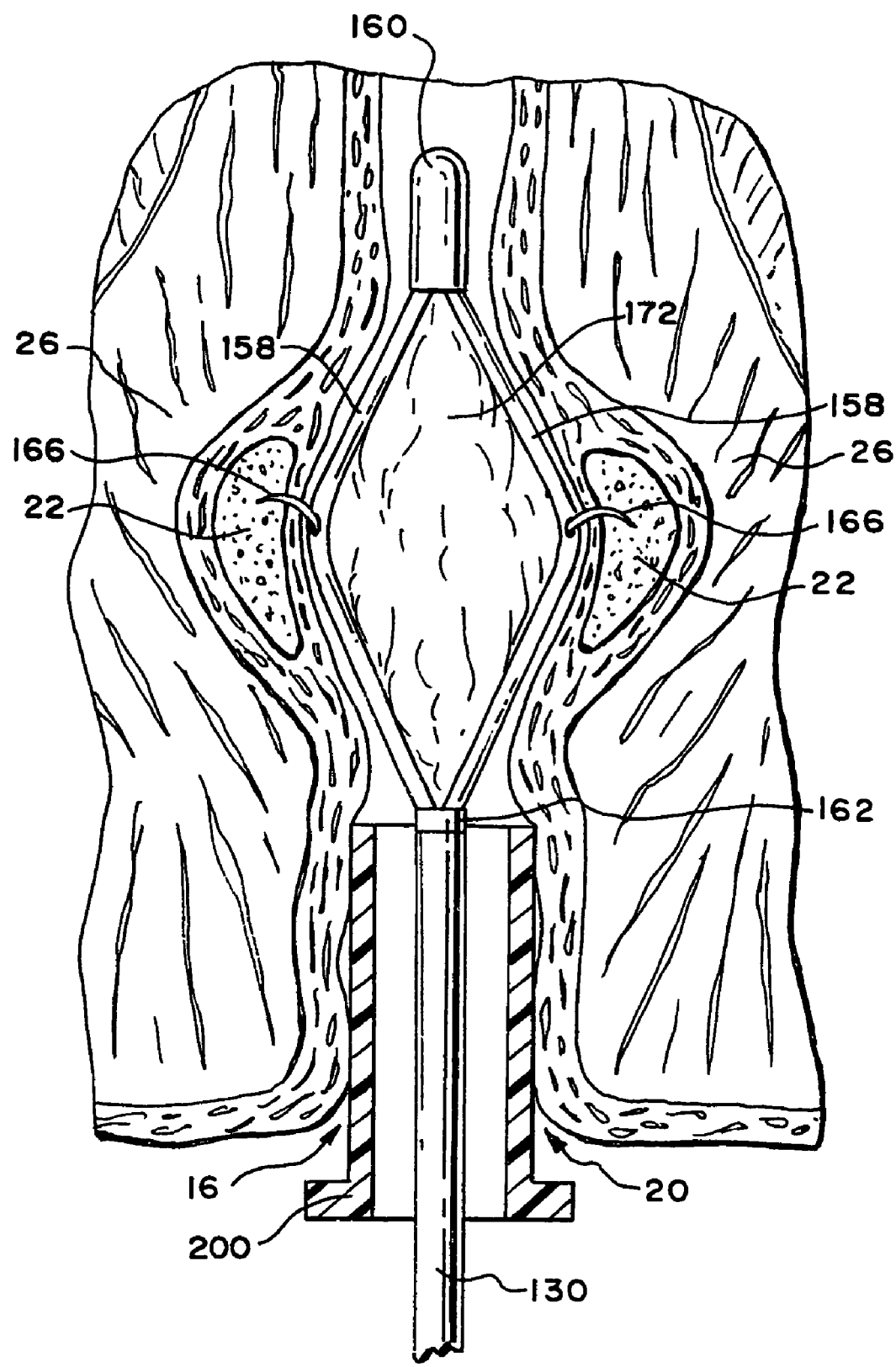
FIG. 17 is an anatomic view of the anal canal, with the treatment device shown in FIGS. 13 and 14, with the expandable structure expanded and the energy application electrodes extended radially into the internal sphincter muscle.

The physician places the basket 156 in its expanded condition and moves the electrodes 166 into their extended position. The electrodes 166 pierce and pass through the mucosal tissue 76 into the targeted muscle tissue, as FIG. 17 shows and as previously described.

The physician commands the controller 64 to apply radio frequency energy through the electrodes 166, to ohmically heat the muscle tissue. The controller 64 can condition the electrodes 166 to operate in a monopolar mode. In this arrangement, each electrode 166 serves as a transmitter of energy, and an indifferent patch electrode (not shown) serves as a common return for all electrodes 166. Alternatively, the controller 64 can condition selected pairs of electrodes 166 to operate in a bipolar mode. In this mode, one of the electrodes 166 comprises the transmitter and another electrode comprises the return for the transmitted energy. The bipolar electrode pairs can comprise electrodes 166 on adjacent spines 138, or electrodes 166 spaced more widely apart on the basket 158.

The controller 64 samples temperatures, using the sensors 180, to control the application of energy. Cooling fluid can also be conveyed through the spines 158, to further control mucosal tissue temperature, as ohmic heating of the targeted underlying muscle tissue occurs.

Once the desired lesions are formed, the physician retracts the electrodes 166 and collapses the basket 156. The catheter tube 130 and basket 156 are withdrawn through the anuscope 200.

The various treatment devices disclosed in this Specification can be supplied to a physician as part of a sterile kit. The kit packages the particular treatment device as a single use item in a sterile fashion within peripherally sealed sheets of plastic film material that are torn or peeled away at the instance of use. The kit can include, together with the particular treatment device or separately supplied, instructions for using the device according to one or more of the methodologies disclosed herein.

Features of the invention are set forth in the following claims.

We claim:

1. A method for treating fecal incontinence comprising
identifying for treatment an anal cavity having a dentate line, anoderm tissue below the dentate line, and anal columns immediately above the dentate line,
providing a transparent structure having a distal end and including an array of tissue-piercing electrodes at the distal end capable of controlled advancement relative to the transparent structure between a retracted position withdrawn in the transparent structure and an advanced position extending outward from the transparent structure,
inserting the transparent structure into the anal cavity with the array of tissue piercing electrodes in the retracted position,
visualizing from outside the anal cavity the dentate line within the anal canal through the transparent structure,
while visualizing the dentate line, locating the distal end of the transparent structure at least about 3 cm above the dentate line,
advancing the array of tissue piercing electrodes from the retracted position to the advanced position into tissue only at or near an anal sphincter at least about 3 cm above the dentate line,
applying energy through the array of tissue-piercing electrodes while in the advanced position to create a lesion in the tissue without thermal damage to anoderm tissue and anal columns in the anal canal, and
conveying fluid into contact with the tissue to cool the tissue while applying energy to the array of tissue-piercing electrodes.

2. A method according to claim 1 wherein the energy applied is radiofrequency energy.

3. A method according to claim 1 further including sensing a tissue temperature condition while applying energy to the array of tissue-piercing electrodes.

* * * * *